US012778732B2

(12) United States Patent
Demarest et al.

(10) Patent No.: US 12,778,732 B2
(45) **Date of Patent: *Nov. 3, 2026**

(54) TEETH WHITENING SYSTEM

(71) Applicant: Colgate-Palmolive Company, New York, NY (US)

(72) Inventors: Scott Demarest, Loudon, TN (US); Stacey Lavender, Chesterfield, NJ (US); Richard Adams, South Orange, NJ (US); Yu Shi, Branchburg, NJ (US)

(73) Assignee: Colgate-Palmolive Company, New York, NY (US)

( * ) Notice: Subject to any disclaimer, the term of this patent is extended or adjusted under 35 U.S.C. 154(b) by 51 days.

This patent is subject to a terminal disclaimer.

(21) Appl. No.: 18/896,988

(22) Filed: Sep. 26, 2024

(65) Prior Publication Data

US 2025/0017713 A1 Jan. 16, 2025

Related U.S. Application Data

(63) Continuation of application No. 16/949,911, filed on Nov. 20, 2020, now Pat. No. 12,109,086, which is a (Continued)

(51) Int. Cl.
*A61C 19/06* (2006.01)
*A61N 5/06* (2006.01)

(52) U.S. Cl.
CPC .......... *A61C 19/066* (2013.01); *A61C 19/063* (2013.01); *A61N 5/0603* (2013.01); (Continued)

(58) Field of Classification Search
CPC .. A61C 19/066; A61C 19/063; A61N 5/0603; A61N 2005/0653; A61N 2005/0606; A61N 2005/0652
(Continued)

(56) References Cited

U.S. PATENT DOCUMENTS 4,968,251 A * 11/1990 Darnell ................ A61C 19/063 433/80
6,602,275 B1 * 8/2003 Sullivan ............... A61N 5/0616 607/90
(Continued)

FOREIGN PATENT DOCUMENTS

CN 1914527 2/2007
CN 201741720 2/2011
(Continued)

OTHER PUBLICATIONS

International Search Report and Written Opinion of the International Searching Authority in International Application No. PCT/US2016/014607, mailed Aug. 1, 2016.

*Primary Examiner* — Matthew M Nelson

(57) ABSTRACT

A teeth whitening system that emits electromagnetic radiation onto surfaces of a user's teeth when a tooth whitening material is in contact with the user's teeth. In one aspect, the teeth whitening system includes a mouthpiece comprising a wall and a bite platform extending from the wall and an electromagnetic radiation source coupled to the mouthpiece and configured to emit electromagnetic radiation onto surfaces of the user's teeth that are positioned in the first channel. The tooth whitening system may alternatively include rupturable bladders containing teeth whitening material.

19 Claims, 13 Drawing Sheets

Related U.S. Application Data continuation of application No. 15/554,082, filed as application No. PCT/US2016/014607 on Jan. 22, 2016, now Pat. No. 10,893,924.

(60) Provisional application No. 62/126,217, filed on Feb. 27, 2015.

(52) U.S. Cl.
CPC ................. *A61N 2005/0606* (2013.01); *A61N 2005/0652* (2013.01); *A61N 2005/0653* (2013.01)

(58) Field of Classification Search
USPC ........................................................... 433/29
See application file for complete search history.

(56) References Cited

U.S. PATENT DOCUMENTS 6,893,259 B1 5/2005 Reizenson
7,114,953 B1* 10/2006 Wagner ................ A61C 19/066 433/214
7,255,691 B2 8/2007 Tolkoff et al.
7,331,784 B2 2/2008 Suzuki
7,572,124 B2* 8/2009 Cipolla ................ A61C 19/004 433/29
7,645,137 B2 1/2010 Wasyluch
7,715,254 B2 5/2010 Kwon
7,717,709 B2 5/2010 Kobayashi
7,802,988 B2 9/2010 Yarborough
7,997,898 B2 8/2011 Ortiz et al.
8,021,148 B2 9/2011 Goodson et al.
8,215,954 B2 7/2012 Levine
8,240,312 B2 8/2012 Feuerstein et al.
8,371,853 B2* 2/2013 Levine ................ A61C 19/066 433/32
8,591,227 B2* 11/2013 Levine ................ A61C 19/066 433/32
8,602,774 B2 12/2013 Wasylucha
8,684,956 B2* 4/2014 McDonough ........ A61C 17/024 433/80
8,809,614 B2 8/2014 Wilhoit
8,940,033 B2* 1/2015 Dwyer ................ A61C 19/066 362/249.02
8,978,659 B2 3/2015 Bardach et al.
9,242,164 B2 1/2016 Maurello
9,259,143 B2 2/2016 Lawrence
9,275,980 B2 3/2016 Groenendaal et al.
9,373,807 B2 6/2016 Pan et al.
9,387,054 B2 7/2016 Hines et al.
9,539,076 B2 1/2017 Almutairi
9,539,438 B2 1/2017 Pan et al.
9,572,645 B2* 2/2017 Levine ...................... A61F 7/00
9,730,780 B2 8/2017 Brawn et al.
9,770,643 B2 9/2017 Hawkins
9,839,500 B2 12/2017 Flyash
9,974,630 B2* 5/2018 Heacock .............. A61C 1/0046
10,245,129 B2 4/2019 Nagayama et al.
10,870,014 B2 12/2020 Demarest et al.
10,893,924 B2 1/2021 Demarest et al.
2001/0046654 A1 11/2001 Zavitsanos et al.
2003/0036037 A1* 2/2003 Zavitsanos ............... A61K 8/22 433/32
2003/0228264 A1* 12/2003 Perna ................... A61C 19/066 424/53
2004/0110111 A1* 6/2004 Wasylucha ........... A61C 19/063 433/29
2005/0048444 A1 3/2005 Creamer
2005/0202363 A1* 9/2005 Osterwalder ........ A61C 19/066 433/29
2005/0244792 A1* 11/2005 Verdi ................... A61C 19/066 433/215
2006/0019214 A1* 1/2006 Lawrence ............ A61C 19/066 433/29
2006/0127837 A1* 6/2006 Nguyen ............... A61C 19/063 433/29
2006/0141422 A1 6/2006 K. Philp, Jr. et al.
2006/0172252 A1* 8/2006 Suzuki ................. A61C 19/066 433/29
2007/0003905 A1* 1/2007 Nguyen ............... A61C 19/003 433/29
2007/0037116 A1* 2/2007 Knutson .............. A61C 9/0006 433/68
2007/0054235 A1* 3/2007 Rizoui ................. A61C 19/066 433/29
2007/0141528 A1* 6/2007 Kobayashi ........... A61B 1/0008 433/29
2008/0032253 A1 2/2008 Montgomery et al.
2008/0063999 A1* 3/2008 Osborn ................ A61C 19/066 433/29
2008/0233541 A1* 9/2008 De Vreese ........... A61C 19/066 433/216
2008/0255498 A1* 10/2008 Houle ................ A61C 17/0205 604/20
2009/0017422 A1* 1/2009 Creamer .............. A61C 19/066 433/215
2009/0074679 A1* 3/2009 Silverman .............. A61Q 11/02 424/53
2009/0181338 A1* 7/2009 Ortiz ........................ A61C 7/08 433/29
2009/0322227 A1* 12/2009 Jones ..................... H05B 45/12 315/76
2010/0028829 A1* 2/2010 Lewis ..................... C08L 83/04 433/80
2010/0179469 A1 7/2010 Hammond et al.
2010/0240013 A1* 9/2010 Levine ................ A61M 35/006 604/290
2011/0076636 A1* 3/2011 Wolff ................... A61C 19/063 433/29
2011/0104631 A1* 5/2011 Levine ................. A61C 19/063 433/29
2011/0189626 A1* 8/2011 Sanzari ................ A61N 5/0603 433/29
2012/0021375 A1* 1/2012 Binner ................... A61B 5/097 433/89
2012/0040307 A1* 2/2012 Postal .................. A61C 19/066 433/89
2012/0214122 A1* 8/2012 Dwyer ................. A61C 19/066 433/29
2012/0258053 A1 10/2012 Patel et al.
2013/0029291 A1* 1/2013 Williams ................ A61F 5/566 128/862
2013/0045457 A1* 2/2013 Chetiar ................ A61C 19/066 433/29
2013/0063023 A1 3/2013 Pan et al.
2013/0087157 A1* 4/2013 Hawkins .............. A63B 71/085 264/16
2013/0183635 A1* 7/2013 Wilhoit ..................... A61F 7/12 433/136
2013/0209954 A1* 8/2013 Prakash ............ A61B 1/00172 433/29
2013/0230822 A1* 9/2013 Hines ....................... A61C 5/82 433/91
2013/0230823 A1* 9/2013 Lawrence ................ A61B 1/24 433/29
2013/0280670 A1* 10/2013 Edgren .................... A61C 7/22 433/22
2013/0280671 A1* 10/2013 Brawn ................. A61N 5/0603 433/29
2014/0014119 A1* 1/2014 Bardach ............... A61C 19/066 128/861
2014/0072932 A1* 3/2014 Brawn ................... A61C 19/06 433/215
2014/0092598 A1* 4/2014 Groenendaal ........... B32B 37/24 362/249.02
2014/0196725 A1* 7/2014 Maurello .................. A61F 5/00 128/861
2014/0272770 A1* 9/2014 Hurley ................. A61N 5/0603 433/29

(56) References Cited

U.S. PATENT DOCUMENTS

| | | | | |
|---|---|---|---|---|
| 2015/0037749 | A1* | 2/2015 | Levine | A61C 19/063<br>433/215 |
| 2015/0044628 | A1* | 2/2015 | Flyash | A61C 19/066<br>433/32 |
| 2015/0132709 | A1* | 5/2015 | Park | A61N 5/0603<br>433/29 |
| 2015/0140502 | A1* | 5/2015 | Brawn | A61C 19/006<br>433/29 |
| 2015/0157434 | A1* | 6/2015 | Bardach | A61J 7/0053<br>433/217.1 |
| 2015/0164618 | A1* | 6/2015 | Heacock | A61C 1/0046<br>433/2 |
| 2016/0113747 | A1* | 4/2016 | Almutairi | A61C 19/066<br>433/80 |
| 2016/0135936 | A1* | 5/2016 | Nagayama | A61C 17/022<br>433/80 |
| 2016/0235511 | A1* | 8/2016 | Kodama | A61C 19/063 |
| 2016/0338810 | A1* | 11/2016 | Schmalhurst | A61C 17/221 |
| 2017/0173353 | A1* | 6/2017 | Demarest | A61C 19/066 |
| 2018/0263746 | A1* | 9/2018 | Demarest | A61C 19/066 |
| 2021/0145559 | A1 | 5/2021 | Demarest et al. | |

FOREIGN PATENT DOCUMENTS

| | | | | | |
|---|---|---|---|---|---|
| CN | 102188294 | | | 9/2011 | |
| CN | 202178253 | | | 3/2012 | |
| CN | 102738375 | | | 10/2012 | |
| CN | 103210490 | | | 7/2013 | |
| CN | 104048196 | | | 9/2014 | |
| CN | 104081532 | | | 10/2014 | |
| CN | 104106149 | | | 10/2014 | |
| DE | 202011104169 | | | 10/2011 | |
| EP | 1054642 | | | 11/2000 | |
| EP | 1649827 | | | 4/2006 | |
| GB | 2522224 | A | * | 7/2015 | A61C 19/066 |
| JP | 2011217983 | | | 11/2011 | |
| KR | 200388592 | Y1 | * | 6/2005 | A61K 8/0208 |
| KR | 200406685 | Y1 | * | 1/2006 | A61C 19/066 |
| KR | 20090094089 | A | * | 9/2009 | A61N 5/06 |
| RU | 2320379 | | | 3/2008 | |
| WO | 2005/009270 | | | 2/2005 | |
| WO | 2006/020128 | | | 2/2006 | |
| WO | 2006/107362 | | | 10/2006 | |
| WO | WO-2006107362 | A1 | * | 10/2006 | A61C 19/063 |
| WO | WO-2008022220 | A2 | * | 2/2008 | A61C 19/003 |
| WO | 2010/098761 | | | 9/2010 | |
| WO | 2010/098764 | | | 9/2010 | |
| WO | WO-2010098764 | A1 | * | 9/2010 | A61N 5/0603 |
| WO | 2011/159522 | | | 12/2011 | |
| WO | 2011/163220 | | | 12/2011 | |
| WO | 2013/093743 | | | 6/2013 | |
| WO | WO-2014017645 | A1 | * | 1/2014 | A61C 7/36 |
| WO | WO-2016032040 | A1 | * | 3/2016 | A61C 19/063 |

* cited by examiner

TEETH WHITENING SYSTEM

CROSS-REFERENCE TO RELATED APPLICATIONS

The present application is a continuation of the U.S. application Ser. No. 16/949,911, filed Nov. 20, 2020, which is a continuation of U.S. patent application Ser. No. 15/554,082, filed Aug. 28, 2017, which is a national stage entry under 35 U.S.C. § 371 of PCT/US2016/014607, filed Jan. 22, 2016, which claims priority to U.S. Provisional Patent Application Ser. No. 62/126,217, filed Feb. 27, 2015, the entireties of which are incorporated herein by reference.

BACKGROUND

Tooth whitening is an increasingly popular treatment and dentists and patients alike are searching for techniques that are both convenient and comfortable. Typically, to whiten a user's teeth a composition containing hydrogen peroxide is applied to the teeth and allowed to remain in contact with the teeth to be bleached for a period of time. Current systems are available that allow a user to apply radiation or light to the surfaces of the teeth that are pre-coated with the whitening composition to enhance the effectiveness of the whitening composition. However, currently available systems are bulky and rigid and undesirable for one or more reasons. Specifically, current systems do not emit radiation or light onto the user's pre-coated teeth uniformly and in a manner that effectively covers the entire tooth surface. Thus, a need exists for a tooth whitening system that is able to effectively emit radiation or light onto a user's teeth.

Additionally, current systems require a user to apply a whitening composition to his or her teeth manually, and then to hold a radiation or light source up to the tooth surfaces for application of radiation or light thereto. With currently available systems, inexperienced or careless users may apply an excessive amount of whitening composition, with the result that the excess must be removed and discarded, wasting time and material. Moreover, the excess material may irritate gums or other tissues not intended to be in contact with large amounts of whitening composition. Thus, there exists a need for a teeth whitening system that dispenses a proper amount of the tooth whitening composition and emits radiation onto surfaces of the user's teeth while having increased efficacy and ease of use.

BRIEF SUMMARY

The present invention may be directed, in one aspect, to a teeth whitening system that emits electromagnetic radiation onto surfaces of the user's teeth. In certain aspects, the electromagnetic radiation is emitted by an electromagnetic radiation source that is coupled to a wall of a mouthpiece. The electromagnetic radiation source may comprise a flexible circuit and a plurality of illumination elements located thereon. In some aspects the electromagnetic radiation source is a printed light emitting diode circuit. In other aspects of the invention, the teeth whitening system may dispense an oral care material into contact with the surfaces of the user's teeth. The oral care material may be a tooth whitening material. The teeth whitening system may include a mouthpiece or other structure that supports the electromagnetic radiation source and that retains the tooth whitening material. Additional electronic components such as a processor and a power source may also be included in the system.

In another aspect, the invention may be a teeth whitening system comprising: a mouthpiece comprising a wall and a bite platform extending from the wall that collectively define a first channel for receiving a user's teeth; an electromagnetic radiation source coupled to the mouthpiece and configured to emit electromagnetic radiation onto surfaces of the user's teeth that are positioned in the first channel; and one or more apertures in at least one of the wall or the bite platform, the one or more apertures configured to dispense a tooth whitening material to the first channel for contact with the surfaces of the user's teeth that are positioned in the first channel.

In yet another aspect, the invention may be a teeth whitening system comprising: a mouthpiece comprising a wall having an inner surface and an opposing outer surface and a bite platform extending from the inner surface of the wall, the wall and the bite guard collectively defining a first channel for receiving a user's teeth; an electromagnetic radiation source coupled to the mouthpiece and configured to emit electromagnetic radiation onto surfaces of the user's teeth that are positioned in the first channel; and an opening formed into the outer surface of the wall and forming a passageway to a distribution manifold located within at least one of the wall and the bite guard, the distribution manifold extending from the opening in the outer surface of the wall to one or more apertures that are configured to dispense a tooth whitening material to the first channel for contact with the surfaces of the user's teeth that are positioned in the first channel.

In a further aspect, the invention may be a teeth whitening system comprising: a mouthpiece comprising a wall and a bite platform extending from the wall that collectively define a first channel for receiving a user's teeth, the bite platform having a cavity for storing a tooth whitening material; an electromagnetic radiation source coupled to the mouthpiece and configured to emit electromagnetic radiation onto surfaces of the user's teeth that are positioned in the first channel; and one or more apertures in at least one of the wall or the bite platform, the one or more apertures fluidly coupled to the tooth whitening material in the cavity, the tooth whitening material being dispensed through the one or more apertures to the first channel for contact with the surfaces of the user's teeth that are positioned in the first channel in response to compression of the bite platform.

In a still further aspect, the invention may be a teeth whitening system comprising: a mouthpiece comprising a wall and a bite platform extending from the wall that collectively define a first channel for receiving a user's teeth; an electromagnetic radiation source coupled to the wall of the mouthpiece, the electromagnetic radiation source comprising a first flexible circuit and a plurality of first illumination elements located on the first flexible circuit, the electromagnetic radiation source configured to emit electromagnetic radiation onto surfaces of the user's teeth that are positioned in the first channel.

In another aspect, the invention may be a teeth whitening system comprising: a mouthpiece comprising a wall and a bite platform extending from the wall, the wall of the mouthpiece comprising an upper wall portion extending upward from the bite platform and a lower wall portion extending downward from the bite platform, the upper wall portion and an upper surface of the bite platform forming a first channel that is configured to receive a user's upper teeth, the lower wall portion and a lower surface of the bite platform forming a second channel that is configured to receive the user's lower teeth, the bite platform being positioned between the user's upper and lower teeth; a first electromagnetic radiation source coupled to the upper wall portion and configured to emit electromagnetic radiation onto surfaces of the user's upper teeth that are positioned in the first channel, a second electromagnetic radiation source coupled to the lower wall portion and configured to emit electromagnetic radiation onto surfaces of the user's lower teeth that are positioned in the second channel; and the first electromagnetic radiation source comprising a first flexible circuit and a plurality of first illumination elements located on the first flexible circuit and the second electromagnetic radiation source comprising a second flexible circuit and a plurality of second illumination elements located on the second flexible circuit.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1A:
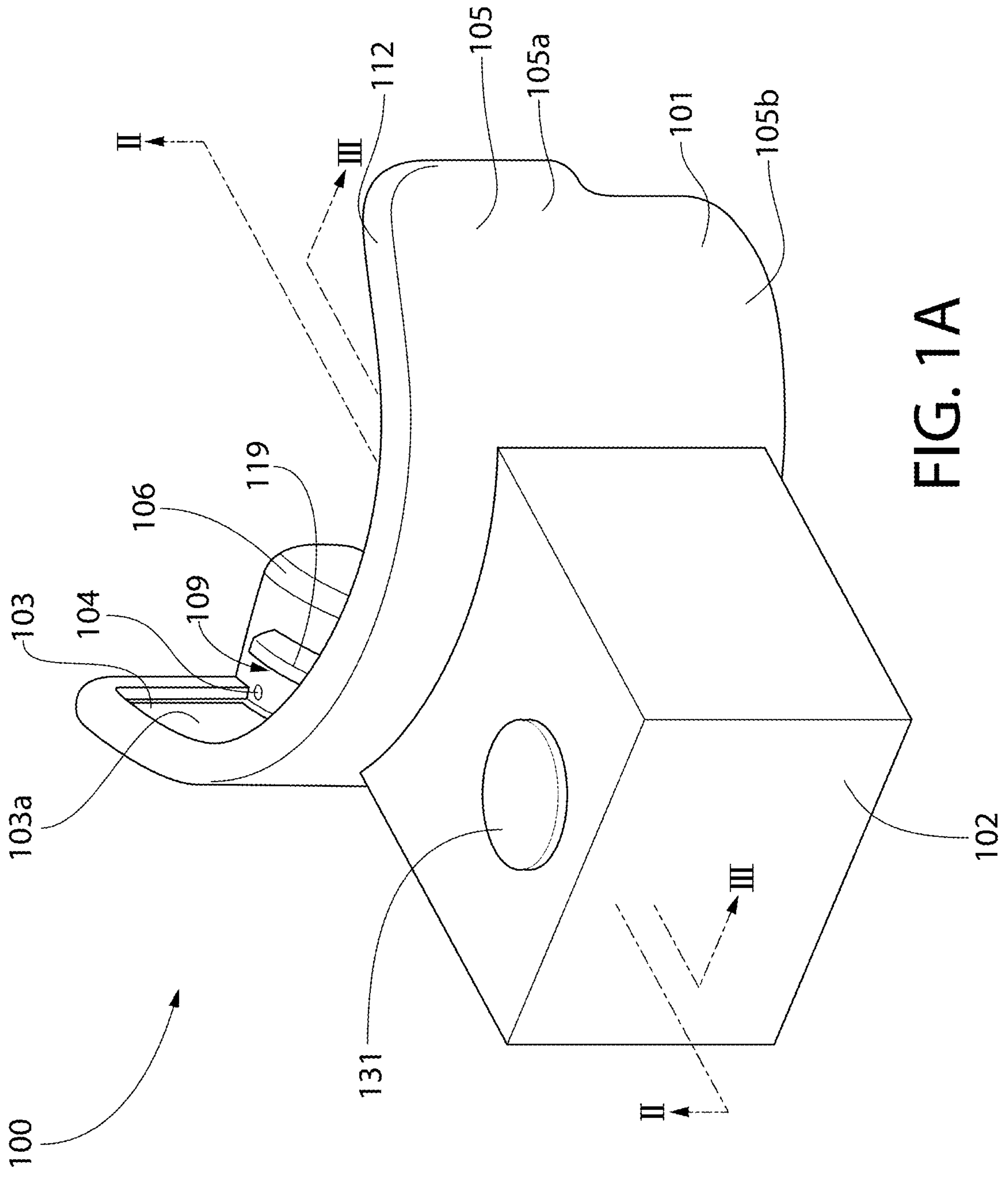
FIG. 1A is a front perspective view of a teeth whitening system in accordance with a first embodiment of the present invention.
Figure 1B:
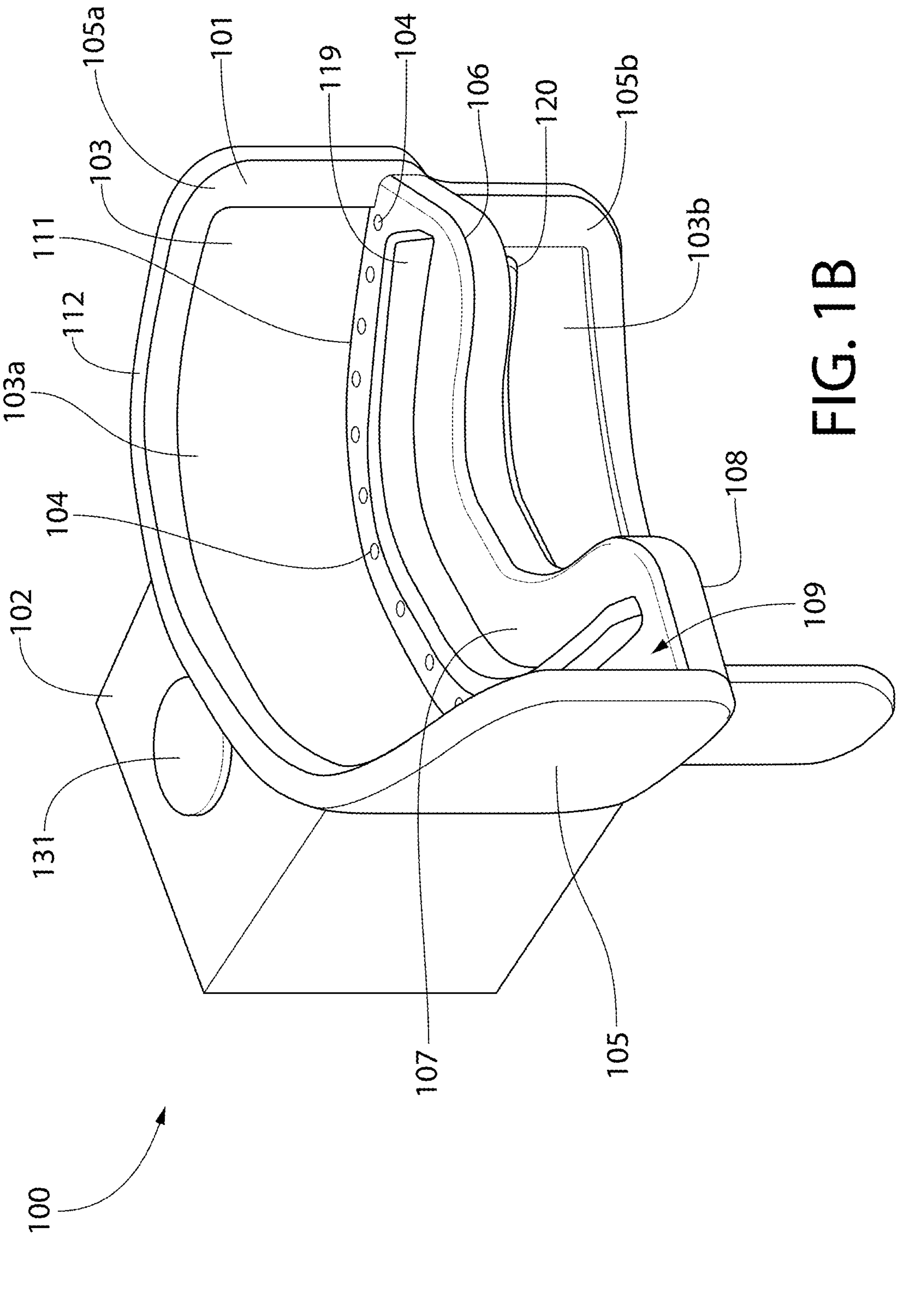
FIG. 1B is a rear perspective view of the teeth whitening system of FIG. 1A.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Referring to FIGS. 1A-3 concurrently, a teeth whitening system 100 will be described in accordance with an embodiment of the present invention. It is known in teeth whitening systems that a more effective whitening result can be achieved by applying a tooth whitening material to a user's teeth and then emitting light or electromagnetic radiation onto the teeth with the tooth whitening material pre-applied thereon in order to activate the tooth whitening material. Many of these systems require that a user manually apply the tooth whitening material to his or her teeth, and then emit the light or electromagnetic radiation onto his or her teeth. In some embodiments of the present disclosure, the teeth whitening system 100 both dispenses the tooth whitening material onto the user's teeth and emits light or electromagnetic radiation onto the user's teeth in a single action (or in automated subsequent actions), thereby reducing the steps necessary for a user to conduct a tooth whitening session and reducing the time it takes for a user to whiten his or her teeth. By being an all-in-one inclusive system, the teeth whitening system 100 of the present invention is readily portable and simple to use.

Although in several embodiments presented herein the invention is described as being a device that both dispenses a tooth whitening material onto a user's teeth and emits light or electromagnetic radiation onto the user's teeth, the invention is not to be limited to such dual-action in all embodiments. Rather, in certain embodiments the tooth whitening system 100 may only emit light or electromagnetic radiation onto the user's teeth without also dispensing a tooth whitening material onto the user's teeth. Thus, the specific details with regard to the tooth whitening material dispensing and the structures and components that achieve the dispensing of the tooth whitening material may be omitted in certain embodiments. In some embodiments the invention is directed to a teeth whitening system that emits electromagnetic radiation onto a user's teeth but does not also dispense a whitening composition. In such an embodiment the teeth whitening system will have all of the components described herein below that are necessary for achieving the generation/transmission of electromagnetic radiation while the components necessary for achieving the whitening composition dispensing are omitted.

In an exemplified embodiment, the teeth whitening system 100 generally comprises a mouthpiece 101, a housing 102 coupled to the mouthpiece 101, an electromagnetic radiation source 103 coupled to the mouthpiece 101, and one or more apertures 104 formed into the mouthpiece 101. The one or more apertures 104 are configured to dispense a tooth whitening material into contact with surfaces of a user's teeth. Thus, in embodiments that do not include tooth whitening material dispensing, the one or more apertures may be omitted. The electromagnetic radiation source 103 is configured to emit electromagnetic radiation onto the surfaces of the user's teeth. The details of the dispensing of tooth whitening material and the emission of electromagnetic radiation on the user's teeth will be described in more detail below.

In certain embodiments, the mouthpiece 101 may be formed of a food grade polymer such as, including without limitation, polyethylene terephthalate (PET), polypropylene (PP), polyethylene naphthalate (PEN), polyethylene (PE), silicone, ethylene propylene diene monomer (EPDM), and other plastics. Of course, the invention is not to be so limited in all embodiments and other materials are possible for construction of the mouthpiece 101. Specifically, in certain embodiments the mouthpiece 101, or at least the bite platform 106 thereof, may be formed of a compressible material, which may be one of the materials noted above, or may be a hard rubber or the like. The mouthpiece 101 is intended to be placed within a user's mouth into contact with the user's oral surfaces and saliva, so the material used to form the mouthpiece 101 should be non-toxic and devoid of foul tastes.

The structure of the mouthpiece 101 will now be described with reference to FIGS. 1A-3. The mouthpiece 101 generally comprises a wall 105 and a bite platform 106 extending from the wall 105. The wall 105 and the bite platform 106 collectively form one or more channels for receiving a user's teeth during a tooth whitening session. More specifically, in the exemplified embodiment the wall 105 of the mouthpiece 101 comprises an upper wall portion **105*a* extending upward from an upper surface 107 of the bite platform 106 and a lower wall portion 105*b* extending downward from a lower surface 108 of the bite platform 106. The upper wall portion 105*a* and the upper surface 107 of the bite platform 106 collectively form a first channel 109 for receiving a user's upper teeth 198 during a tooth whitening session and the lower wall portion 105*b* and the lower surface 108 of the bite platform 106 collectively form a second channel 110 for receiving a user's lower teeth 199 during a tooth whitening session. During use, the mouthpiece 101 is inserted into a user's mouth such that the bite platform 106 is trapped or sandwiched between the user's upper and lower teeth 198, 199, the upper wall portion 105*a* of the wall 105 faces the front surfaces of the user's upper teeth 198, and the lower wall portion 105*b* of the wall 105 faces the front surfaces of the user's lower teeth 199**.

The upper wall portion **105*a* extends from a proximal end 111 that is coupled to the bite platform 106 to a distal end 112. Furthermore, the upper wall portion 105*a* comprises an inner surface 113 that faces the user's teeth when the mouthpiece 101 is in use and an opposing outer surface 114. The inner surface 113 of the upper wall portion 105*a* has a recess formed therein. More specifically, a first portion 116 of the inner surface 113 of the upper wall portion 105*a* extends from the bite platform 106 to a shoulder 117 of the upper wall portion 105*a* and a second portion 118 of the inner surface 113 of the upper wall portion 105*a* extends from the shoulder 117 to the distal end 112 of the upper wall portion 105*a*. The first portion 116 of the inner surface 113 of the upper wall portion 105*a* is recessed relative to the second portion 118 of the inner surface 113 of the upper wall portion 105*a*. Stated another way, the upper wall portion 105*a* has a first thickness T1 measured between the outer surface 114 of the upper wall portion 105*a* and the first portion 116 of the inner surface 113 of the upper wall portion 105*a* and a second thickness T2 measured between the outer surface 114 of the upper wall portion 105*a* and the second portion 118 of the inner surface 113 of the upper wall portion 105*a*. The second thickness T2 is greater than the first thickness T1**.

Figure 3:
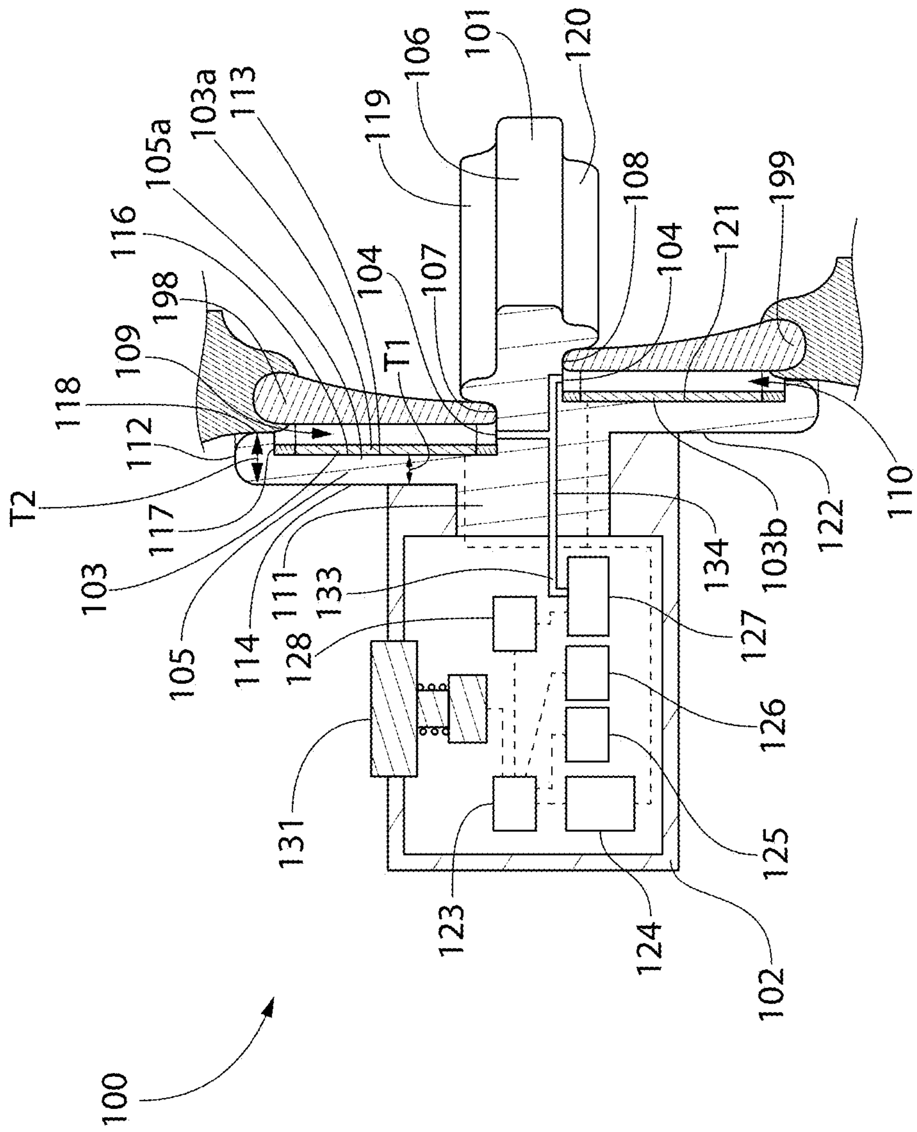
FIG. 3 is a cross-sectional view taken along line III-III of FIG. 1A, wherein a user's teeth are engaged with the mouthpiece.

The lower wall portion **105*b* has an inner surface 121 and an opposing outer surface 122. The inner surface 121 of the lower wall portion 105*b* has a recess similar to the recess of the upper wall portion 105*a* described above. Generally, the structure of the lower wall portion 105*b* is the same as the structure of the upper wall portion 105*a* and it will not be repeated herein in the interest of brevity. As can be seen in the embodiment of FIG. 3, the inner surfaces 113, 121 of the upper and lower wall portions 105*a*, 105*b* of the wall 105 are offset from one another. Thus, a longitudinal axis that runs centrally through the upper wall portion 105*a* from the proximal end 111 to the distal end 112 will not intersect the lower wall portion 105*b*. This is done in the exemplified embodiment to enhance the comfort of the mouthpiece 101 during use due to the general shape of a user's bite (with the upper teeth positioned forward of the lower teeth). Of course, the invention is not to be so limited in all embodiments and the inner surfaces 113, 121 of the upper and lower wall portions 105*a*, 105*b* need not be offset in all embodiments. Despite being offset in the exemplified embodiment, the inner surfaces 113, 121 of the upper and lower wall portions 105*a*, 105*b*** are substantially parallel to one another.

The bite platform 106 extends from the wall 105 to a distal or terminal end. The inner surface 113 of the upper wall portion **105*a* is located a first distance from the distal end of the bite platform 106 and the inner surface 121 of the lower wall portion 105*b* is located a second distance from the distal end of the bite platform 106, the first distance being greater than the second distance. Furthermore, the outer surface 122 of the lower wall portion 105*b* is offset from the inner surface 116 of the upper wall portion 105***a*, the inner surface 116 of the upper wall portion 105*a* being positioned a greater distance from the distal end of the bite platform 106 than the outer surface 122 of the lower wall portion 105*b*.

The structure of the upper and lower wall portions 105*a*, 105*b* of the wall 105 facilitate the formation of the first and second channels 109, 110. Specifically, with regard to the upper wall portion 105*a*, when the mouthpiece 101 is properly inserted into a user's mouth, the second portion 118 of the inner surface 113 of the upper wall portion 105*a* contacts the user's gums that are adjacent to the user's upper teeth 198. Because the first portion 116 of the inner surface 113 of the upper wall portion 105*a* is recessed relative to the second portion 118 of the inner surface 113 of the upper wall portion 105*a*, the user's teeth 198 are spaced apart from the first portion 116 of the inner surface 113 of the upper wall portion 105*a* by the first channel 109. Thus, the first channel 109 provides a location within which a tooth whitening material (or any other desired oral care agent) can be dispensed into contact with the user's teeth during a tooth whitening (or other type of oral care treatment) regimen in embodiments that include a dispensing feature.

In the exemplified embodiment, the inner surface 113 of the upper wall portion 105*a* has a concave shape that corresponds or is complementary to the collective shape of the front or labial/buccal surfaces of the user's top teeth 198 and the inner surface 121 of the lower wall portion 105*b* has a concave shape that corresponds or is complementary to the collective shape of the front or labial/buccal surfaces of the user's bottom teeth 199. More specifically, the inner surface 113 of the upper wall portion 105*a* has a shape that corresponds to at least a portion of the maxillary arch of the user's teeth and the inner surface 121 of the lower wall portion 105*b* has a shape that corresponds to at least a portion of the mandibular arch of the user's teeth. Similarly, the first channel 109 has an arcuate or curved shape that corresponds to the shape of the maxillary arch of the user's teeth and the second channel 110 has an arcuate or curved shape that corresponds to the shape of the mandibular arch of the user's teeth. This enhances the conformance of the mouthpiece 101 to a user's mouth during use.

The bite platform 106 extends from the wall 105 at a location between the upper and lower wall portions 105*a*, 105*b* of the wall 105. In the exemplified embodiment the bite platform 106 and the wall 105 connect at an approximately 90° angle, although the invention is not to be so limited in all embodiments and other angles of connection between the bite platform 106 and the wall 105 are possible in other embodiments. The bite platform 106 forms a horizontal biting surface for the user to engage with his or her teeth 198, 199 to retain the mouthpiece 101 in a desired position within the user's mouth during a treatment session.

The bite platform 106 comprises a first ridge 119 extending upwardly from the upper surface 107 of the bite platform 106 and a second ridge 120 extending downwardly from the lower surface 108 of the bite platform 106. In the exemplified embodiment, each of the first and second ridges 119, 120 are elongated and arcuate shaped protrusions that extend from the bite platform 106 in opposite directions. Furthermore, in the exemplified embodiment the first ridge 119 is a curved ridge having a curvature that matches the collective curvature of the rear surfaces (i.e., lingual surfaces) of the user's upper teeth and the second ridge 120 is a curved ridge having a curvature that matches the collective curvature of the rear surfaces (i.e., lingual surfaces) of the user's lower teeth. Of course, the invention is not to be so limited in all embodiments and the first and second ridges 119, 120 need not be elongated or arcuate in all embodiments. Specifically, in some embodiments the first and second ridges 119, 120 may be formed by a plurality of discrete protuberances rather than being a single continuous ridge.

The first ridge 119 is spaced apart from the upper wall portion 105*a* by a gap (i.e., by at least a portion of the first channel 109) and the second ridge 120 is spaced apart from the lower wall portion 105*b* by a gap (i.e., by at least a portion of the second channel 110). In the exemplified embodiment, the gap between the first ridge 119 and the upper wall portion 105*a* and the gap between the second ridge 120 and the lower wall portion 105*b* have the same width so that when the mouthpiece 101 is inserted into a user's mouth, the spacing between the user's upper teeth and the upper wall portion 105*a* is identical to the spacing between the user's lower teeth and the lower wall portion 105*b*.

The first ridge 119 provides a structure for the rear surfaces of the user's upper teeth 198 to rest against during use of the mouthpiece 101 and the second ridge 120 provides a structure for the rear surfaces of the user's lower teeth 199 to rest against during use of the mouthpiece 101. Thus, when the user inserts the mouthpiece 101 into his or her mouth, the user will know exactly where to position the teeth on the mouthpiece 101 based on the location of the first and second ridges 119, 120 in order to ensure that adequate spacing between the teeth and the wall 105 is achieved so that the tooth whitening material can be dispensed into the first and second channels 109, 110. As can be seen in FIG. 3, in the exemplified embodiment the first and second ridges 119, 120 are offset from one another. This is done in the exemplified embodiment to enhance user comfort because the offset nature of the first and second ridges 119, 120 imitates the offset nature of the user's upper and lower teeth (typically a user's upper teeth extend further forward towards the front of the mouth than the user's lower teeth). Of course, in still other embodiments the first and second ridges 119, 120 may be altogether omitted and proper spacing between the user's teeth and the wall 105 can be achieved by the recessed structure of the portions of the wall 105 as described herein above.

Although the invention is illustrated and described herein such that it includes the upper and lower wall sections 105*a*, 105*b*, the invention is not to be so limited in all embodiments. In certain other embodiments, the mouthpiece 101 may include the bite platform 106 and only one of the upper and lower wall sections 105*a*, 105*b*. In this manner, one mouthpiece that includes the bite platform 106 and the upper wall section 105*a* can be used for treating the user's upper teeth. A separate mouthpiece that includes the bite platform 106 and the lower wall section 105*b* can be used for treating the user's lower teeth. Thus, an alternative embodiment includes two separate mouthpieces, one for treatment of the upper teeth and one for treatment of the lower teeth. This alternative embodiment may be advantageous when it is desired to only treat the upper teeth or the lower teeth, but can also be used to treat both the upper and lower teeth simultaneously. Thus, the mouthpiece 101 can be a single integral structure for treating the upper and lower teeth simultaneously or two separate structures, one for treating the upper teeth and another for treating the lower teeth.

Still referring to FIGS. 1A-3, as noted above the teeth whitening system 100 further comprises the electromagnetic radiation source 103 coupled to the mouthpiece. In the exemplified embodiment, the electromagnetic radiation source 103 comprises a first electromagnetic radiation source 103*a* coupled to the upper wall portion 105*a* and a second electromagnetic radiation source 103*b* coupled to the lower wall portion 105*b*. More specifically, in the exemplified embodiment the first electromagnetic radiation source 103*a* is coupled to the first portion 116 of the inner surface 113 of the upper wall portion 105*a* such that the first electromagnetic radiation source 103*a* is located within the recess of the upper wall portion 105*a*. Similarly, in the exemplified embodiment the second electromagnetic radiation source 103*b* is coupled to the inner surface 121 of the lower wall portion 105*b* such that the second electromagnetic radiation source 103*b* is located within the recess of the lower wall portion 105*b*. Of course, the invention is not to be so limited in all embodiments and the first electromagnetic radiation source 103*a* may be coupled to the upper surface 107 of the bite platform 106 in some embodiments and/or the second electromagnetic radiation source 103*b* may be coupled to the lower surface 108 of the bite platform 106 in some embodiments. In other embodiments, the first electromagnetic radiation source 103*a* may be coupled to the upper surface 107 of the bite platform 106 and the upper wall portion 105*a* and the second electromagnetic radiation source 103*b* may be coupled to the lower surface 108 of the bite platform 106 and the lower wall portion 105*b*.

Although the first electromagnetic radiation source 103*a* is positioned within the recess of the upper wall portion 105*a*, the exposed outer surface of the first electromagnetic radiation source 103*a* remains recessed relative to the second portion 118 of the inner surface 113 of the upper wall portion 105*a*. This ensures that a space remains between the user's teeth 198 and the first electromagnetic radiation source 103*a* so that the tooth whitening material that is either dispensed by the device or pre-coated onto the teeth can be located within the space during the whitening regimen. The same is true of the second electromagnetic radiation source 103*b* in that it is recessed relative to the second portion of the inner surface 121 of the lower wall portion 105*b*.

The electromagnetic radiation source 103 is coupled to the mouthpiece 101 in such a manner that it can emit electromagnetic radiation onto the surfaces of the user's teeth 198, 199 when the user's teeth 198, 199 are positioned within the first and second channels 109, 110. Specifically, when the mouthpiece 101 is properly positioned within a user's mouth, the user's upper teeth 198 are located within the first channel 109 and the user's lower teeth 199 are located within the second channel 110. In this position, the electromagnetic radiation source 103 can properly emit electromagnetic radiation onto surfaces of the user's teeth 198, 199. In the exemplified embodiment, the first and second electromagnetic radiation sources 103*a*, 103*b* are coupled to the inner surfaces 113, 121 of the upper and lower wall portions 105*a*, 105*b*, respectively. Thus, the first and second electromagnetic radiation sources 103*a*, 103*b* are curved so as to have concave surfaces that face the user's teeth when the mouthpiece 101 is positioned within the user's mouth. During use, the first and second electromagnetic radiation sources 103*a*, 103*b* are configured to emit the electromagnetic radiation onto the front surfaces (i.e., the labial/buccal surfaces) of the user's upper and lower teeth 198, 199, respectively. In certain embodiments, the first and second electromagnetic radiation sources 103*a*, 103*b* are configured to emit the electromagnetic radiation orthogonally into contact with surfaces of the user's upper and lower teeth 198, 199 (i.e., at an approximately 90° angle). Of course, electromagnetic radiation can be emitted onto other surfaces or portions of the user's upper and lower teeth 198, 199 depending on the portion of the mouthpiece 101 to which the first and second electromagnetic radiation sources 103*a*, 103*b* are coupled as described herein above.

In certain embodiments, the first and second electromagnetic radiation sources 103*a*, 103*b* may be enclosed within the mouthpiece 101 such that a portion of the mouthpiece 101 covers the first and second electromagnetic radiation sources 103*a*, 103*b*. Thus, the electromagnetic radiation sources 103*a*, 103*b* may not be exposed, but rather may be protected by the portions of the mouthpiece 101 which may protect the electromagnetic radiation sources 103*a*, 103*b* against damage from saliva and the teeth. In such embodiments, the portion of the mouthpiece 101 that covers the first and second electromagnetic radiation sources 103*a*, 103*b* may be transparent or translucent to permit the electromagnetic radiation emitted by the first and second electromagnetic radiation sources 103*a*, 103*b* to pass therethrough.

Figure 2:
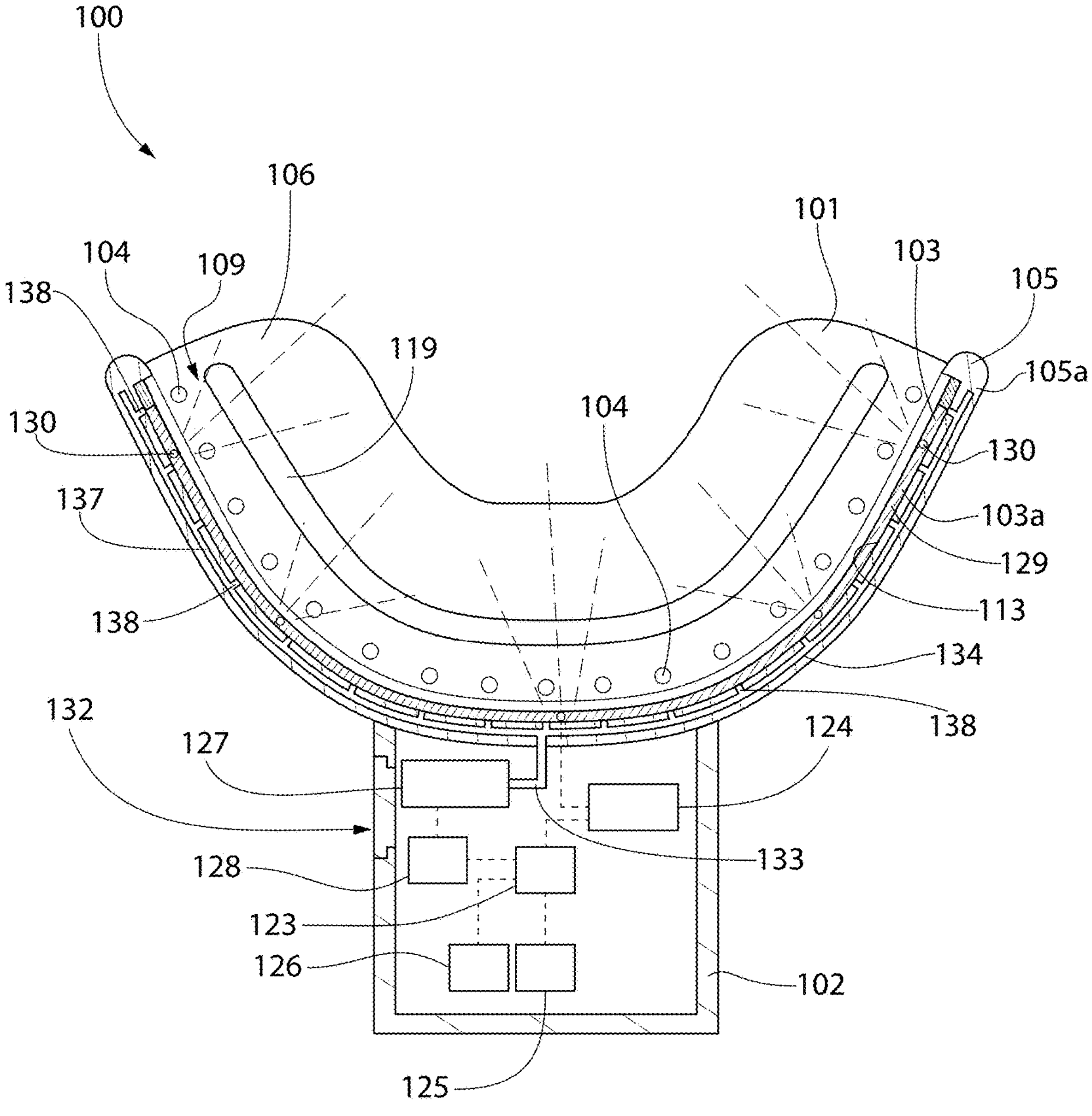
FIG. 2 is a cross-sectional view taken along line II-II of FIG. 1A illustrating an electromagnetic radiation source coupled to a mouthpiece and emitting electromagnetic radiation.

The electromagnetic radiation source 103 (and more specifically, each of the first and second electromagnetic radiation sources 103*a*, 103*b*) can be any type of electromagnetic radiation source 103 desired that emits electromagnetic radiation when power is supplied thereto. In certain embodiments, the electromagnetic radiation source 103 comprises a first flexible circuit 129 with a plurality of first illumination elements 130 thereon (FIG. 2). In the exemplified embodiment only a few of the first illumination elements 130 are labeled to avoid clutter, and only a few of the first illumination elements 130 are depicted transmitting light, although it should be appreciated that most, or all, of the first illumination elements 130 would transmit light during use. In certain exemplified embodiments the plurality of first illumination elements 130 are light emitting diodes (LEDs), and the terms illumination elements and LEDs may be used interchangeably herein. Although described herein as being LEDs, the first illumination elements 130 may in certain embodiments be any type of light source, particularly solid state light sources, which may include LEDs, OLEDs, HBLEDs, electroluminescent elements, or the like.

The first flexible circuit 129 may be a flat, flexible substrate or sheet that appears to glow when power is provided thereto. The first flexible circuit 129 may have flat, planar opposing major surfaces (i.e., front and rear surfaces). Furthermore, in certain embodiments the first flexible circuit 129 of the electromagnetic radiation source 103 may be a printed light emitting diode. Printed LEDs may be formed by depositing micro LED chips via a conductive ink formulation that can be printed in any shape to best conform to the teeth and jaw structure, which is ideal for optimized efficacy. Specifically, gallium nitride may be used to form the LEDs in some embodiments, which may then be mixed with resin and binders to form an ink, and a standard screen printer may be used to deposit the resulting ink over a desired surface. The substrate or first flexible circuit 129 can be a thin plastic film or paper and can be formed to match the contours of the mouthpiece 101. In certain embodiments, it is merely desirable that the electromagnetic radiation source 103 be electrically conductive, flexible, and able to conform closely to the contours of the teeth. In that regard, the electromagnetic radiation source 103 can be printed inorganic LEDs, micro conventional LEDs that are surface mounted to a flexible substrate/circuit, organic LEDs (OLEDs), or electroluminescence. In still other embodiments, the electromagnetic radiation source 103 can be any of the LEDs noted herein mounted to a rigid rather than a flexible substrate. In certain embodiments, the electromagnetic radiation source 103 is configured to emit electromagnetic radiation in the range of 385 nm to 520 nm, although the invention is not to be so limited and electromagnetic radiation outside of the above-noted range is also possible. In the exemplified embodiment, many of the first illumination elements 130 are illustrated positioned on or embedded within the first flexible circuit 129. In some embodiments there may be thousands or even millions of the first illumination elements 130 positioned on or embedded within the first flexible circuit 129. Because of the large number of first illumination elements 130 formed on or embedded within the first flexible circuit 129, even if some of the first illumination elements 130 burn out or are non-operable, the electromagnetic radiation source 103 will still be capable of operating effectively for tooth whitening. The invention is not to be limited by the number of the first illumination elements 130 in all embodiments, but it is desirable in certain embodiments that the number of the first illumination elements 130 is sufficient to ensure electromagnetic radiation is emitted onto each tooth in the manner described herein.

In the exemplified embodiment, the teeth whitening system 100 further comprises the housing 102 coupled to the mouthpiece 101. In the exemplified embodiment the housing 102 extends from the wall 105 of the mouthpiece 101 in a first direction and the bite platform 106 extends from the wall 105 of the mouthpiece in a second direction that is opposite to the first direction. Thus, the bite platform 106 extends from the inner surfaces 113, 121 of the wall 105 and the housing 102 extends from the outer surfaces 114, 122 of the wall 105 (it should be appreciated that the shoulder 117 described above also extends from the inner surfaces 113, 121 of the wall 105 in the same direction as the bite platform 106). In the exemplified embodiment, the housing 102 is depicted generically as a box. However, the invention is not to be so limited and the shape of the housing 102 can be modified into any desired shape for aesthetic or functional reasons.

In the exemplified embodiment, within the housing 102 is positioned a processor 123, a power supply 124, a timer 125, a heater 126, a reservoir 127, and a pump or pressurizer 128 that are operably coupled together. More specifically, the processor 123 is operably coupled to each of the power source 124, the timer 125, the heater 126, and the pump/pressurizer 128, and the pump/pressurizer 128 is operably coupled to the reservoir 127. The processor 123 may be any suitable microprocessor based programmable logic controller, personal computer, or the like that has memory for storing various instructions to control the operation of the electromagnetic radiation source 103 and the dispensing of a tooth whitening material (or other oral care fluid) from the reservoir 127 as described in more detail below. The processor 123 is programmed with algorithms to receive data from the various other electrical components and sensors, analyze the data, and cause the electrical components to operate in a desired or predetermined manner based on instructions that are stored in the memory of the processor 123. Of course, in embodiments that do not comprise a dispensing function, some or all of the components noted above, such as the pump/pressurizer 128 and the reservoir 127, may be omitted.

In the exemplified embodiment, the power source 124 is operably coupled to the processor 123 and to the electromagnetic radiation source 103 (and more specifically to each of the first and second electromagnetic radiation sources 103*a*, 103*b*). The electrical connections between the various electrical components, and particularly between the power source 124 and the electromagnetic radiation source 103, is illustrated in the figures in dotted lines. The power source 124 may be one or more batteries, battery cells, printed batteries, rechargeable batteries, super capacitors, or a control circuit that store electrical energy that can be used to power the electromagnetic radiation source 103 as desired. Alternatively, the power source 124 may be omitted and instead the electronic components of the device may be powered by a plug that is coupled to a power supply, such as a wall socket.

In the exemplified embodiment, the teeth whitening system 100 also comprises an actuator 131. In the exemplified embodiment, the actuator 131 is a depressible button. However, the invention is not to be so limited and the actuator 131 can be any type of device that upon actuation powers on and/or off one or more of the electrical components stored within the housing 102. For example, the actuator 131 can be a slide switch, a touch pad, or any other component that upon actuation causes the teeth whitening system 100 to function as described herein below. The actuator 131 is operably coupled to the processor 123 so that upon depressing or otherwise actuating the actuator 131, the processor 123 initiates operation of the teeth whitening system 100 as described in more detail below.

As noted above, in embodiments in which the teeth whitening system 100 includes a dispensing feature/function, the reservoir 127 stores the tooth whitening material (i.e., hydrogen peroxide, carbamide peroxide, calcium peroxide, sodium perborate, or the like) or any other oral care fluid that is desired to be dispensed into contact with the user's teeth during use of the mouthpiece 101. As an example of a use of the device different than tooth whitening, the mouthpiece 101 may be used to desensitize the teeth or perform some other desired treatment to the teeth, and the oral care fluid stored in the reservoir 127 can be modified to meet the needs of the treatment system. The tooth whitening material (or other oral care fluid) may be a liquid or a gel and may have varying viscosities selected to achieve a desired dispensing thereof. In certain embodiments, the reservoir 127 may include no more than a single dose of the tooth whitening material. Thus, it should be appreciated that the reservoir 127 may be a replaceable or refillable reservoir 127. In certain embodiments as depicted in FIG. 2, the housing 102 may include an access panel 132 that provides access to the reservoir 127 within the housing 102. In that regard, upon opening or removing the access panel 132, a user can remove the reservoir 127 for refilling or replacement, or can simply refill the reservoir 127 without removal thereof. In other embodiments, the reservoir 127 may include multiple doses of the tooth whitening material, but may be configured to dispense only a single dose at a time, as described in more detail below.

As noted above, in embodiments that include a tooth whitening material dispensing function, the teeth whitening system 100 comprises one or more apertures 104 formed into the mouthpiece 101. More specifically, the teeth whitening system 100 comprises a plurality of the apertures 104. In the exemplified embodiment, a plurality of the apertures 104 are formed into the upper surface 107 of the bite platform 106 and a plurality of the apertures 104 are formed into the lower surface 108 of the bite platform 106. The apertures 104 are formed into the bite platform 106 at a location that is adjacent to the wall 105 to ensure that tooth whitening material dispensed through the apertures 104 come into contact with surfaces of the user's teeth that are positioned within the first and second channels 109, 110. Furthermore, in the exemplified embodiment the plurality of apertures 104 on the upper surface 107 of the bite platform 103 are positioned in an evenly spaced-apart manner and the plurality of apertures 104 on the lower surface 108 of the bite platform 106 are positioned in an evenly spaced-apart manner. Of course, the apertures 104 need not be evenly spaced apart in all embodiments and different spacing between the adjacent apertures 104 may be utilized depending on the surface area of the particular tooth that will be positioned near that aperture 104 during use.

Furthermore, although the apertures 104 are illustrated in the drawings as being formed along the bite platform 106, the invention is not to be so limited in all embodiments. In some embodiments, one or more of the apertures 104 may be formed into the inner surfaces 113, 121 of the upper and lower wall portions 105*a*, 105*b*. In certain embodiments, the apertures 104 may only be formed into the inner surfaces 113, 121 of the upper and lower wall portions 105*a*, 105*b* and not also in the bite platform 106. In other embodiments the apertures 104 may be formed into the inner surfaces 113, 121 of the upper and lower wall portions 105*a*, 105*b* and also in the bite platform 106. Regardless of the particular location(s) of the apertures 104, the apertures 104 should be positioned so as to dispense the tooth whitening material (or other oral care fluid) into the first and second channels 109, 110 that are formed between the user's upper and lower teeth 198, 199 and the upper and lower wall portions 105*a*, 105*b*. The apertures 104 may be omitted in embodiments that do not include a dispensing function.

In the exemplified embodiment, the teeth whitening system 100 includes an inlet port 133 that is in fluid communication with the one or more apertures 104 and is configured to be detachably coupled to an outlet of the reservoir 127. Thus, attaching and/or detaching the reservoir 127 for replacement or refilling of the reservoir 127 is achieved by coupling the reservoir 127 to and decoupling the reservoir 127 from the inlet port 133. In one particular embodiment, the reservoir 127 may have a puncturable outlet formed by a rubber material or a film, and the inlet port 133 may terminate at a piercing point. In such embodiment, when the reservoir 127 is properly coupled to the inlet port 133, the inlet port 133 will pierce open the puncturable outlet of the reservoir 127 to facilitate the fluid coupling therebetween. Of course, the invention is not to be so limited in all embodiments and the coupling and decoupling of the reservoir 127 to/from the inlet port 133 can be achieved in any of various known manners as would be appreciated by persons of ordinary skill in the art.

As noted above, the inlet port 133 is fluidly coupled to the one or more apertures 104. More specifically, in the exemplified embodiment the inlet port 133 is fluidly coupled directly to a distribution manifold 134, and the distribution manifold 134 is in turn fluidly coupled directly to each of the plurality of apertures 104. The distribution manifold 134 may be considered to comprise the inlet port 133, a distribution chamber 137, and a plurality of outlet ports 138, each of the outlet ports 138 extending from the distribution chamber 137 to one of the apertures 104. The distribution manifold 134 may be located within the bite platform 106, within the wall 105, or partially within the bite platform 106 and partially within the wall 105. In the exemplified embodiment, a fluid path exists from the reservoir 127, through the inlet port 133 to the distribution manifold 134, and from the distribution manifold 134 to each of the apertures 104 for delivery/dispensing of the tooth whitening material into contact with the user's teeth. Thus, in certain exemplified embodiments, the teeth whitening system 100 is capable of both dispensing a tooth whitening material into contact with the user's teeth and emitting electromagnetic radiation onto the user's teeth. As described above, in other embodiments the teeth whitening system 100 may be capable of emitting electromagnetic radiation on the user's teeth that may or may not be pre-coated with a tooth whitening material. In such embodiments the teeth whitening system 100 may not dispense a tooth whitening material into contact with the user's teeth.

Figure 4:
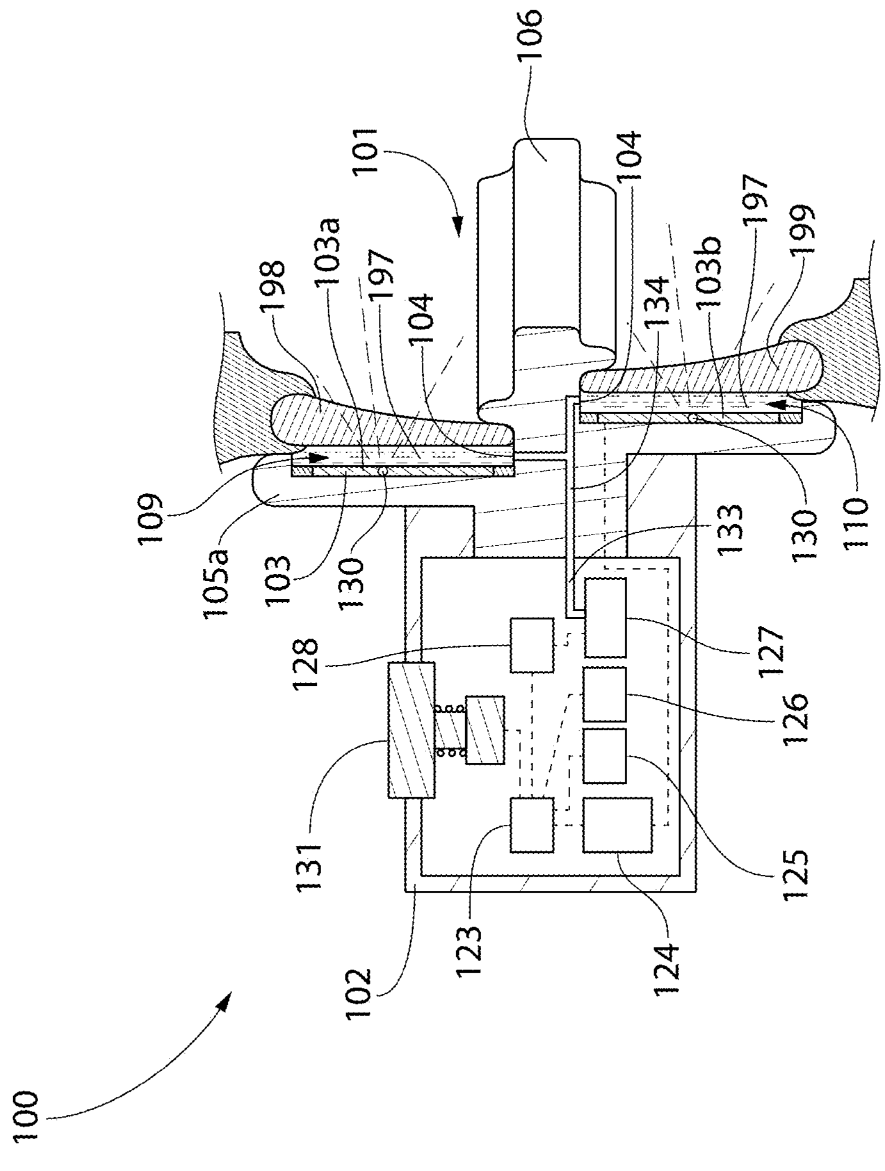
FIG. 4 is the cross-sectional view illustrated in FIG. 3, wherein a tooth whitening material is located within a channel between the user's teeth and the mouthpiece.

The use of the teeth whitening system 100 will now be described with reference to FIGS. 2-4. First, the mouthpiece 101 is positioned within a user's mouth so that the user's upper teeth 198 are adjacent to the upper wall portion 105*a* of the wall 105 and are in contact with the upper surface 107 of the bite platform 106 and the user's lower teeth 199 are adjacent to the lower wall portion 105*b* of the wall 105 and are in contact with the lower surface 108 of the bite platform 106. Thus, as seen in FIGS. 3 and 4, the bite platform 106 is sandwiched between the user's upper and lower teeth 198, 199. Next, the user actuates the actuator 131, which may be achieved, for example without limitation, by depressing an actuator button. Actuation of the actuator 131 will result in the processor 123 instructing the power source 124 to transmit power to the electromagnetic radiation source 103 and instructing the pump/pressurizer 128 to dispense the tooth whitening material from the reservoir 127 to the apertures 104. Although a single actuator 131 is illustrated in the exemplary embodiment, the invention is not to be so limited. In certain other embodiments a first actuator may be provided for controlling the electromagnetic radiation source 103 and a second actuator may be provided for controlling the dispensing functionality of the teeth whitening system 100.

In certain embodiments, upon actuation of the actuator 131, the electromagnetic radiation source 103 will begin immediately emitting electromagnetic radiation and the reservoir 127 will begin immediately dispensing the tooth whitening material. Thus, in such embodiment the electromagnetic radiation will be emitted simultaneously with the dispensing of the tooth whitening material. However, in other embodiments there may be a delay in one of the two functions. Specifically, in one particular embodiment, upon actuation of the actuator 131 the processor 123 will instruct the reservoir 127 (directly or via the pump/pressurizer 128) to immediately begin dispensing a dose of the tooth whitening material. However, in one such embodiment the processor 123 will wait until a part of or an entirety of the dose of the tooth whitening material 197 has been dispensed before instructing the power source 124 to power the electromagnetic radiation source 103 for emitting the electromagnetic radiation. In this manner, the electromagnetic radiation source 103 will not begin emitting the electromagnetic radiation until the user's teeth are coated, covered, or otherwise contacted with the tooth whitening material 197. In still other embodiments actuation of the actuator 131 will result in the electromagnetic radiation source 103 emitting the electromagnetic radiation, but will not also result in any dispensing function.

Regardless of which particular functionality is used, when the processor 123 instructs the reservoir 127 to dispense the tooth whitening material 197, the pump/pressurizer 128 or other appropriate mechanism will cause the tooth whitening material 197 to flow from the reservoir 127, through the inlet port 133 to the distribution manifold 134, through the distribution manifold 134 to and through each of the apertures 104 and into the first and second channels 109, 110. As noted above, the processor 123 may be preconfigured with instructions that enable the processor 123 to cause only a single dose of the tooth whitening material 197 to be dispensed upon a single actuation of the actuator 131. Thus, even if the reservoir 127 stores multiple doses of the tooth whitening material 197 only a single dose will be dispensed at a time. This simplifies use in that the user need not determine the appropriate amount of the tooth whitening material 197 to use, but rather the teeth whitening system 100 automatically makes such determination and dispenses the appropriate amount of the tooth whitening material 197 to the appropriate locations of the user's teeth.

Due to the particular location of the apertures 104, upon reaching and being dispensed through the apertures 104, the tooth whitening material 197 will be located within the first channel 109 that is formed between the user's upper teeth 198 and the upper wall portion 105*a* and the second channel 110 that is formed between the user's lower teeth 199 and the lower wall portion 105*b*, as depicted in FIG. 4. Specifically, the tooth whitening material 197 will pass through the apertures 104 (which may include one or more first apertures that are configured to dispense the tooth whitening material into the first channel 109 and one or more second apertures that are configured to dispense the tooth whitening material into the second channel 110) and fill the first and second channels 109, 110. An appropriate dose will be determined based on the viscosity of the tooth whitening material 197, the width of the first and second channels 109, 110 (i.e., the distance between the teeth 198, 199 and the upper and lower wall portions 105*a*, 105*b*), the flow rate during dispensing, and the like. The appropriate dose will ensure that all of the teeth that are desired to be whitened/treated are coated, covered, or otherwise contacted with the tooth whitening material 197 or other oral care fluid.

When the tooth whitening material 197 is located within the first channel 109, the tooth whitening material 197 will contact surfaces (more particularly front/facial/labial/buccal surfaces) of the user's teeth that are positioned within the first channel 109. When the tooth whitening material 197 is located within the second channel 110, the tooth whitening material 197 will contact surfaces (more particularly front/facial/labial/buccal surfaces) of the user's teeth that are positioned within the second channel 110.

Either simultaneous with the dispensing, on a delay after the dispensing as noted herein above, or by itself without any dispensing, the processor 123 will instruct the power source 124 to transmit power to the electromagnetic radiation source 103, and in response the first and second electromagnetic radiation sources 103*a*, 103*b* will emit electromagnetic radiation onto the user's teeth 198, 199. Due to the positioning of the first and second electromagnetic radiation sources 103*a*, 103*b* relative to the user's teeth 198, 199, the first electromagnetic radiation source 103*a* will emit electromagnetic radiation onto the surfaces of the user's upper teeth 198 that are pre-coated with the tooth whitening material 197 and the second electromagnetic radiation source 103*b* will emit electromagnetic radiation onto the surfaces of the user's lower teeth 199 that are pre-coated with the tooth whitening material 197.

In certain embodiments, upon instructing the power source 124 to provide power to the first and second electromagnetic sources 103*a*, 103*b*, the timer 125 will begin counting to keep track of the amount of time that the first and second electromagnetic sources 103*a*, 103*b* are emitting electromagnetic radiation to the user's teeth. It may be desirable to emit the electromagnetic radiation onto the user's teeth for a predetermined amount of time, such as for example between 1 and 30 minutes, or between 5 and 20 minutes, or the like. The preferred amount of time may be dependent on the strength of the tooth whitening material 197, the strength or wattage of the electromagnetic radiation, and other similar factors. In certain embodiments the predetermined amount of time can be programmed into the processor 123 and may be changed by the user.

The timer 125 will keep track of the amount of time that the electromagnetic radiation is being emitted. After the predetermined amount of time has expired as calculated by the timer 125, the timer 125 will transmit signals to the processor 123 to inform the processor 123 that the predetermined amount of time has been reached and the processor 123 will stop the power source 124 from transmitting power to the first and second electromagnetic sources 103*a*, 103*b*. The teeth whitening system 100 may include a visual or audio alarm to inform the user when the treatment time has expired. The processor 123 may be configured to ensure that the electromagnetic radiation is emitted continuously or in a pulsing (on/off) manner throughout the predetermined period of time. Furthermore, it should be appreciated that in certain embodiments the timer 125 may be omitted and the user may manually power the electromagnetic radiation sources 103*a*, 103*b* on and off by actuating the actuator 131 a first time to power on and a second time to power off after a treatment has been completed. Thus, the functionalities of the teeth whitening system 100 described herein are possible to be performed automatically in some embodiments and manually in other embodiments.

Furthermore, in certain embodiments it may be desirable to maintain a certain temperature during oral treatment sessions. Specifically, in certain embodiments the tooth whitening material may be most effective when heated to a temperature of between 37° C. and 47° C., and more specifically approximately 42° C. The electromagnetic radiation source 103 may emit some heat while emitting electromagnetic radiation. Furthermore, the processor 123 may be configured to cause the heater 126 to power on and off as necessary to maintain the desired temperature. Various sensors, such as temperature sensors or the like, may be included in the teeth whitening system 100 and operably coupled to the processor 123 to assist the processor 123 in determining when to power on and off the heater 126 to maintain an optimal working temperature of the tooth whitening material or other oral care fluid.

Figure 5A:
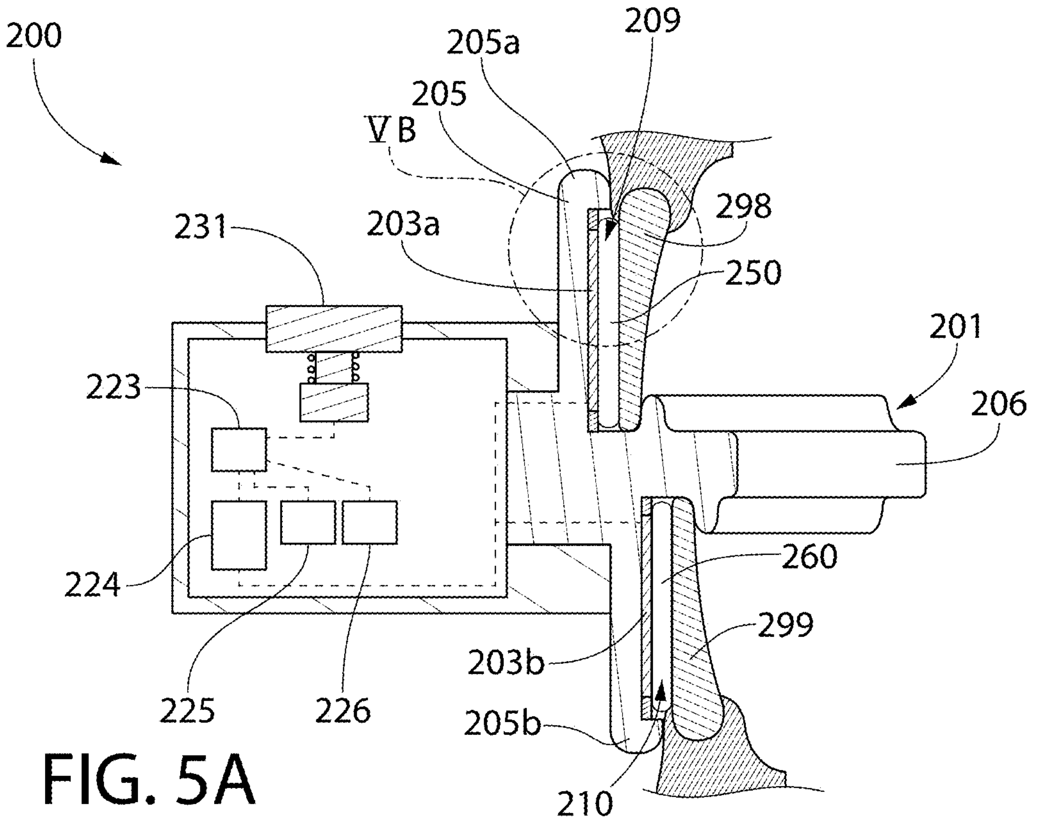
FIG. 5A is a first alternative cross-sectional view taken along line III-III of FIG. 1A, wherein a bladder containing the tooth whitening material is located between a front surface of the user's teeth and the mouthpiece.
Figure 5B:
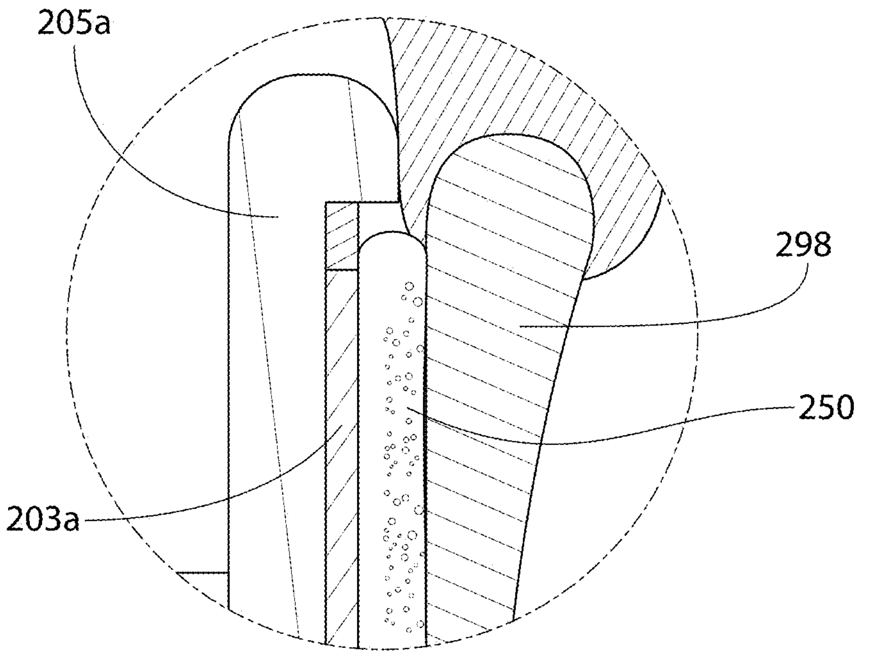
FIG. 5B is a close-up of area VB of FIG. 5A, wherein the bladder is dissolving to dispense the tooth whitening material for contact with the user's teeth.

Referring now to FIGS. 5A and 5B, a teeth whitening system 200 will be described in accordance with another embodiment of the present invention. The teeth whitening system 200 is similar to the teeth whitening system 100 described above. Thus, features of the teeth whitening system 200 that are similar to features of the teeth whitening system 100 will be similarly numbered except that the 200-series of numbers will be used. Certain features of the teeth whitening system 200 that have already been described above with regard to the teeth whitening system 100 will not be described herein below in the interest of brevity, it being understood that the description of the teeth whitening system 100 provided above applies. Thus, for features of the tooth whitening system 200 that are numbered but not described, the description of the similar feature of the tooth whitening system 100 applies.

The teeth whitening system 200 generally comprises a mouthpiece 201, a housing 202 extending from the mouthpiece 201, and first and second electromagnetic radiation sources 203*a*, 203*b* coupled to the upper and lower wall portions 205*a*, 205*b* of the wall 205 of the mouthpiece 201. The structure of the mouthpiece 201 and the housing 202 are the same as that described above with regard to the mouthpiece 101 and the housing 102. Furthermore, the details of the first and second electromagnetic radiation sources 203*a*, 203*a* are the same as that described above. The housing 202 houses the electrical components including a processor 223, a power supply 224, a timer 225, a heater 226, and an actuator 231 that are operably coupled together to facilitate operation of the device. Thus, in this embodiment there is no reservoir or pump mechanism for storing the tooth whitening material. Rather, in this embodiment the tooth whitening material is stored within a first bladder 250 and a second bladder 260 that are separate and distinct from the mouthpiece 201 and housing 202. Although described and illustrated herein as being separate first and second bladders 250, 260, in some embodiments the first and second bladders 250, 260 may be formed as a single bladder.

Each of the first and second bladders 250, 260 can be any type of structure that is compatible for retaining the tooth whitening material until it is desired to dispense the same. Thus, the first and second bladders 250, 260 can be a sealed bag, a pod, a tray, or any other structure capable of sealing the tooth whitening material until its application onto a user's teeth is desired. In this embodiment, when it is desired to use the teeth whitening system 200, a user positions the first bladder 250 within the first channel 209 and the second bladder 250 within the second channel 210. The user then puts the mouthpiece 201 into his or her mouth so that the user's teeth are positioned adjacent to and potentially in contact with the first and second bladders 250, 260. Specifically, in the exemplified embodiment the first bladder 250 is positioned between the front surfaces of the user's upper teeth 298 and the first electromagnetic radiation source 203*a* and the second bladder 260 is positioned between the front surfaces of the user's lower teeth 299 and the second electromagnetic radiation source 203*b*. In this position the user is prevented from puncturing the bladders 250, 260 because the teeth 298, 299 are unable to enter into the first and second channels 209, 210 due to the structure of the upper and lower wall portions 205*a*, 205*b* as described above.

The first and second bladders 250, 260 may be shaped to closely resemble the maxillary and mandibular arches of the user's teeth. The tooth whitening material is sealed within the first and second bladders 250, 260 to ensure shelf-life and barrier requirements of the chemistry. The first and second bladders 250, 260 may be die-cut and thin at the exit points, thereby creating a hybrid slit-score. By having fracture points the tooth whitening material is dispensed in a consistent stream at the desired location in a repeatable and consistent manner. The first and second bladders 250, 260 may be thermoformed, vacuum formed, blow molded, or injection molded in various embodiments.

Referring to FIG. 5B, in this particular embodiment the first and second bladders 250, 260 may be formed of a dissolvable material so that during use, saliva in the user's mouth and on the user's teeth causes the first and second bladders 250, 260 to dissolve so that the tooth whitening material retained therein can be dispensed into the first and second channels 209, 210 and into contact with the user's teeth 298, 299. Thus, in this embodiment the mouthpiece 101 is positioned within the user's mouth. Over time, the first and second bladders 250, 260 will dissolve and the tooth whitening material will fill the first and second channels 209, 210 and contact the user's teeth 298, 299. The user can then actuate the actuator 231, which in turn will cause the processor 223 to instruct the power source 224 to supply power to the first and second electromagnetic radiation sources 203*a*, 203*b* so that they emit electromagnetic radiation onto the surfaces of the user's teeth 298, 299 that are coated with the tooth whitening material. The timer 225 and the processor 223 may monitor the operating time and automatically shut down power to the first and second electromagnetic radiation sources 203*a*, 203*b* after the treatment time has been reached in the manner described above.

Figure 6A:
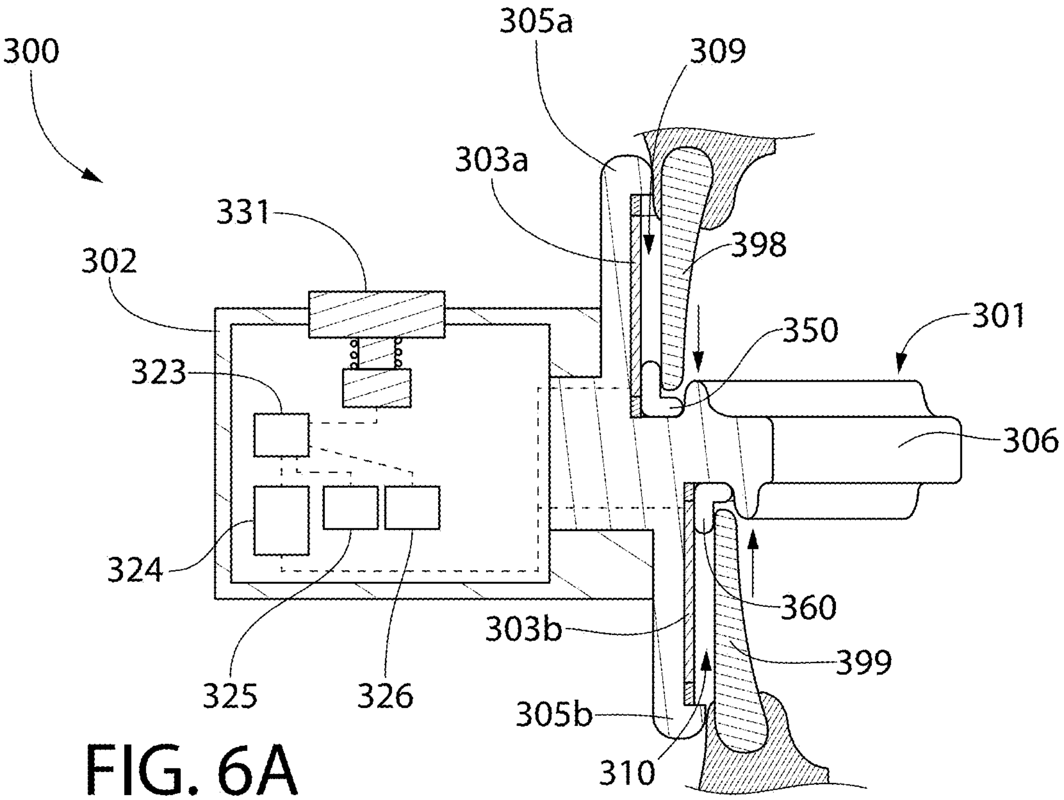
FIG. 6A is a second alternative cross-sectional view taken along line III-III of FIG. 1A, wherein a bladder containing the tooth whitening material is trapped between a bottom edge of the user's teeth and the mouthpiece.
Figure 6B:
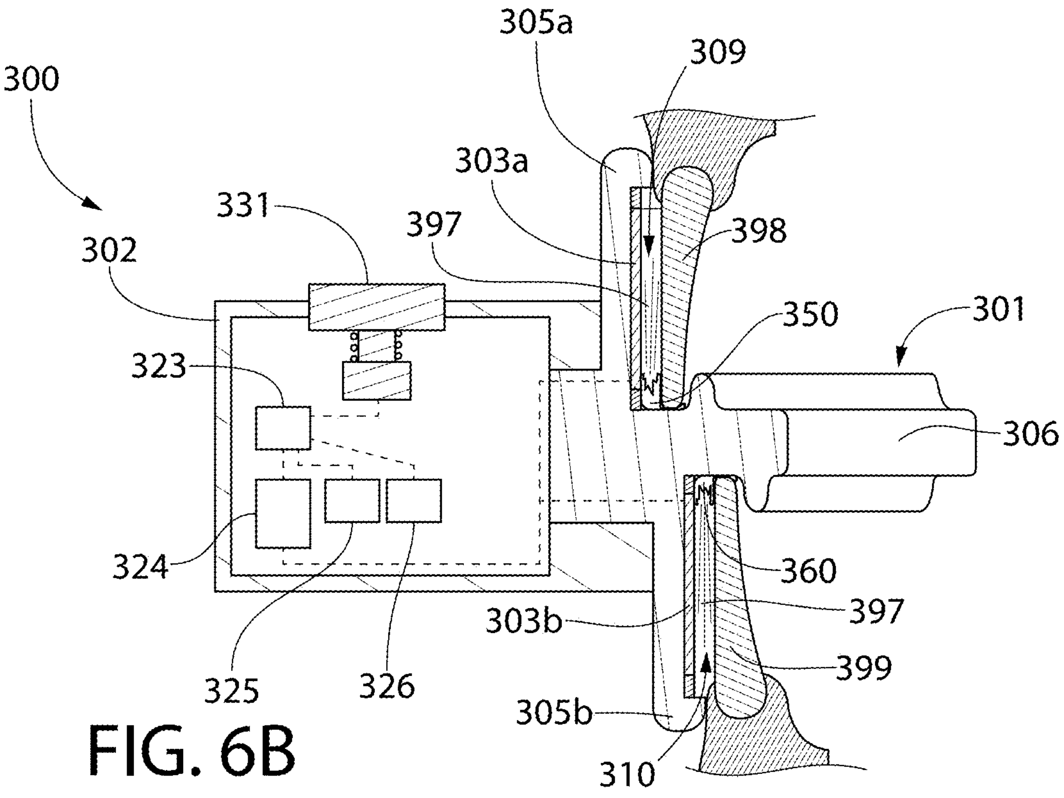
FIG. 6B is the cross-sectional view of FIG. 6A, wherein the bladder has ruptured to dispense the tooth whitening material for contact with the user's teeth.

Referring briefly to FIGS. 6A and 6B concurrently, a teeth whitening system 300 will be described in accordance with yet another embodiment of the present invention. The teeth whitening system 300 is similar to the teeth whitening systems 100, 200 that have already been described herein above. Thus, similar features will be similarly numbered except that the 300-series of numbers will be used. Certain features of the teeth whitening system 300 that have already been described above with regard to the teeth whitening systems 100, 200 will not be described herein below in the interest of brevity, it being understood that the description of the teeth whitening systems 100, 200 provided above applies. Thus, for features of the tooth whitening system 300 that are numbered but not described, the description of the similar feature of the tooth whitening systems 100, 200 applies.

The teeth whitening system 300 is identical to the teeth whitening system 200 except with regard to the positioning of the first and second bladders 350, 360 and the puncturing of the same. Specifically, in this embodiment the first bladder 350 is positioned at least partially between an edge of the user's tooth 398 and the bite platform 306 and the second bladder 360 is positioned at least partially between an edge of the user's tooth 399 and the bite platform 306. Furthermore, in this embodiment rather than dissolving, the first and second bladders 350, 360 are punctured by the user's teeth when the user bites down on the bite platform 306. Specifically, upon biting down on the bite platform 306, the user's teeth 398, 399 in combination with the bite platform 306 will puncture or break open the first and second bladders 350, 360, which will cause the tooth whitening material 397 to be dispensed into the first and second channels 309, 310 and into contact with the user's teeth 398, 399 that are positioned in those channels 309, 310. All other features of the teeth whitening system 200 are applicable to the teeth whitening system 300 and will not be described herein again in the interest of brevity.

Figure 7A:
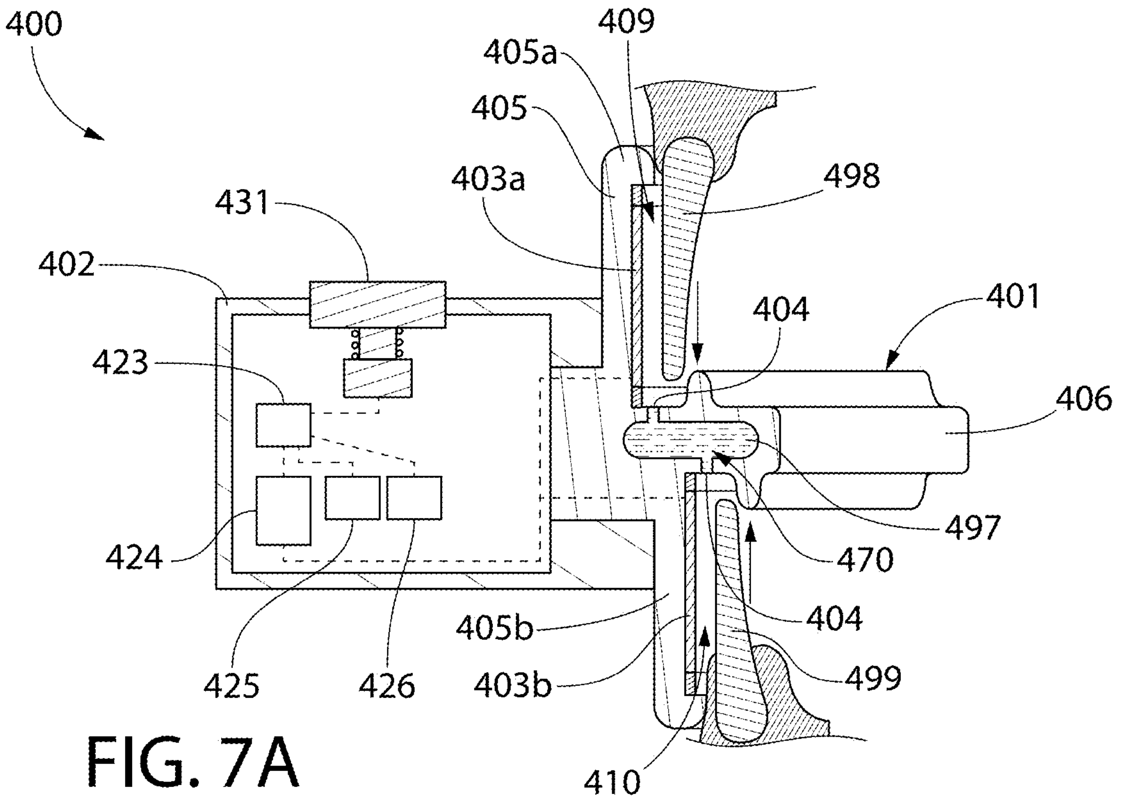
FIG. 7A is a third alternative cross-sectional view taken along line III-III of FIG. 1A, wherein the mouthpiece has a cavity for storing the tooth whitening material.
Figure 7B:
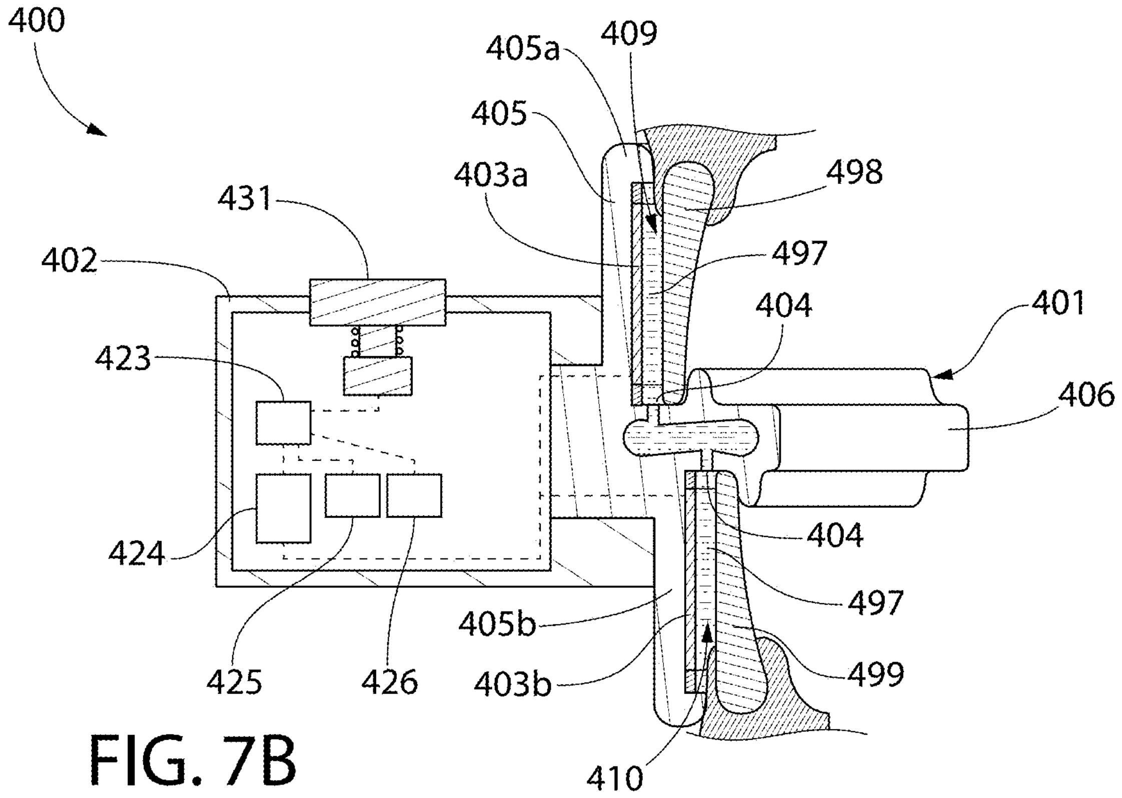
FIG. 7B is the cross-sectional view of FIG. 7A, wherein the tooth whitening material is being dispensed from the cavity.

Referring now to FIGS. 7A and 7B concurrently, a teeth whitening system 400 will be described in accordance with another embodiment of the present invention. The teeth whitening system 400 is similar to the teeth whitening systems 100, 200, 300 described herein above. Thus, features of the teeth whitening system 400 that are similar to features of the teeth whitening systems 100, 200, 300 will be similarly numbered except that the 400-series of numbers will be used. Certain features of the teeth whitening system 400 that have already been described above with regard to the teeth whitening systems 100, 200, 300 will not be described herein below in the interest of brevity, it being understood that the description of the teeth whitening systems 100, 200, 300 provided above applies. Thus, for features of the tooth whitening system 400 that are numbered but not described, the description of the similar feature of the tooth whitening systems 100, 200, 300 applies.

The teeth whitening system 400 generally comprises a mouthpiece 401, a housing 402 coupled to and extending from the mouthpiece 401, and first and second electromagnetic radiation sources 403*a*, 403*b* coupled to the mouthpiece 401. The mouthpiece 401 comprises a wall 405 comprising an upper wall portion 405*a* and a lower wall portion 405*b*, and a bite platform 406 extending from the wall 405 between the upper and lower wall portions 405*a*, 405*b*. The electrical components located within the housing 402 include an actuator 431, a processor 423, a power source 424, a timer 425, and a heater 426 that are operably coupled together in the manner described herein above with regard to the teeth whitening system 100.

In this embodiment, the housing 402 does not also house a reservoir and pump system. Rather, in this embodiment the bite platform 406 comprises a cavity 470 for storing the tooth whitening material 497. Specifically, the bite platform 406 has a hollowed out interior portion that defines the cavity 470. The bite platform 406 may have an inlet port or other opening that provides access into the cavity 470 so that the cavity 470 can be refilled when empty. In certain embodiments, the cavity 470 is sized to hold a single dose of the tooth whitening material 497 at a time.

The teeth whitening system 400 further comprises one or more, and preferably a plurality of apertures 404. In the exemplified embodiment, a plurality of apertures 404 are formed into an upper surface of the bite platform 406 and a plurality of apertures 404 are formed into a lower surface of the bite platform 406. Of course, the apertures 404 can be located at other positions, such as on one or both of the upper and lower wall portions 405*a*, 405*b* or the like. Regardless of the particular positioning of the apertures 404, each of the apertures 404 is fluidly coupled to the tooth whitening material 497 in the cavity 470 so that the tooth whitening material 497 can be dispensed from the cavity 470 through the one or more apertures 404 to the first and second channels 409, 410 for contact with the surfaces of the user's teeth 498, 499 that are positioned within the first and second channels 409, 410.

More specifically, in this embodiment the bite platform 406 is preferably formed out of a compressible material, such as a compressible rubber, plastic, foam, or other type of material. Therefore, during use the mouthpiece 101 is inserted into the user's mouth so that the user's upper teeth 498 are in contact with the upper surface of the bite platform 406 and the user's lower teeth 499 are in contact with the lower surface of the bite platform 406. When it is desired to dispense the tooth whitening material 497, the user will bite down on the bite platform 406 with the upper and lower teeth 498, 499 to compress the bite platform 406. Compression of the bite platform 406 in this manner will cause the tooth whitening material 497 to flow from the cavity 470 through the apertures 404 to be dispensed into the first and second channels 409, 410 and into contact with the user's upper and lower teeth 498, 499. FIG. 7A illustrates the mouthpiece 401 within the user's mouth prior to compression of the bite platform 406 and FIG. 7B illustrates the mouthpiece 401 within the user's mouth during/after compression of the bite platform 406. As can be seen in FIG. 7B, the tooth whitening material 497 is flowing from the cavity 470 through the apertures 404 and into the first and second channels 409, 410 for contact with the user's teeth 498, 499.

In the exemplified embodiment, the tooth whitening material is positioned directly into the cavity 470. However, it can be appreciated that in certain embodiments the tooth whitening material can first be positioned within a bladder (such as the various types of bladders described above with reference to FIGS. 5A-6B), and the bladder can be positioned within the cavity 470. This can ensure that the tooth whitening material is not prematurely dispensed without compression. Specifically, in such embodiments compression of the bite platform 406 will break the bladder to enable the tooth whitening material 497 to flow through the apertures 404 and into the first and second channels 409, 410 for contact with the user's upper and lower teeth 498, 499.

Furthermore, in this embodiment, at any time before, during, or after dispensing of the tooth whitening material, the electromagnetic radiation sources 403*a*, 403*b* can be made to emit electromagnetic radiation onto the surfaces of the user's teeth 498, 499. Specifically, this can be achieved by the user actuating the actuator 431 or in any of the other manners described herein above with regard to the other embodiments. All of the functionalities of the electrical components with regard to providing power to the electromagnetic radiation sources 403*a*, 403*b* and keeping track of the amount of time that the electromagnetic radiation sources 403*a*, 403*b* are emitting electromagnetic radiation described above with regard to the teeth whitening system 100 is applicable to this embodiment.

Figure 8:
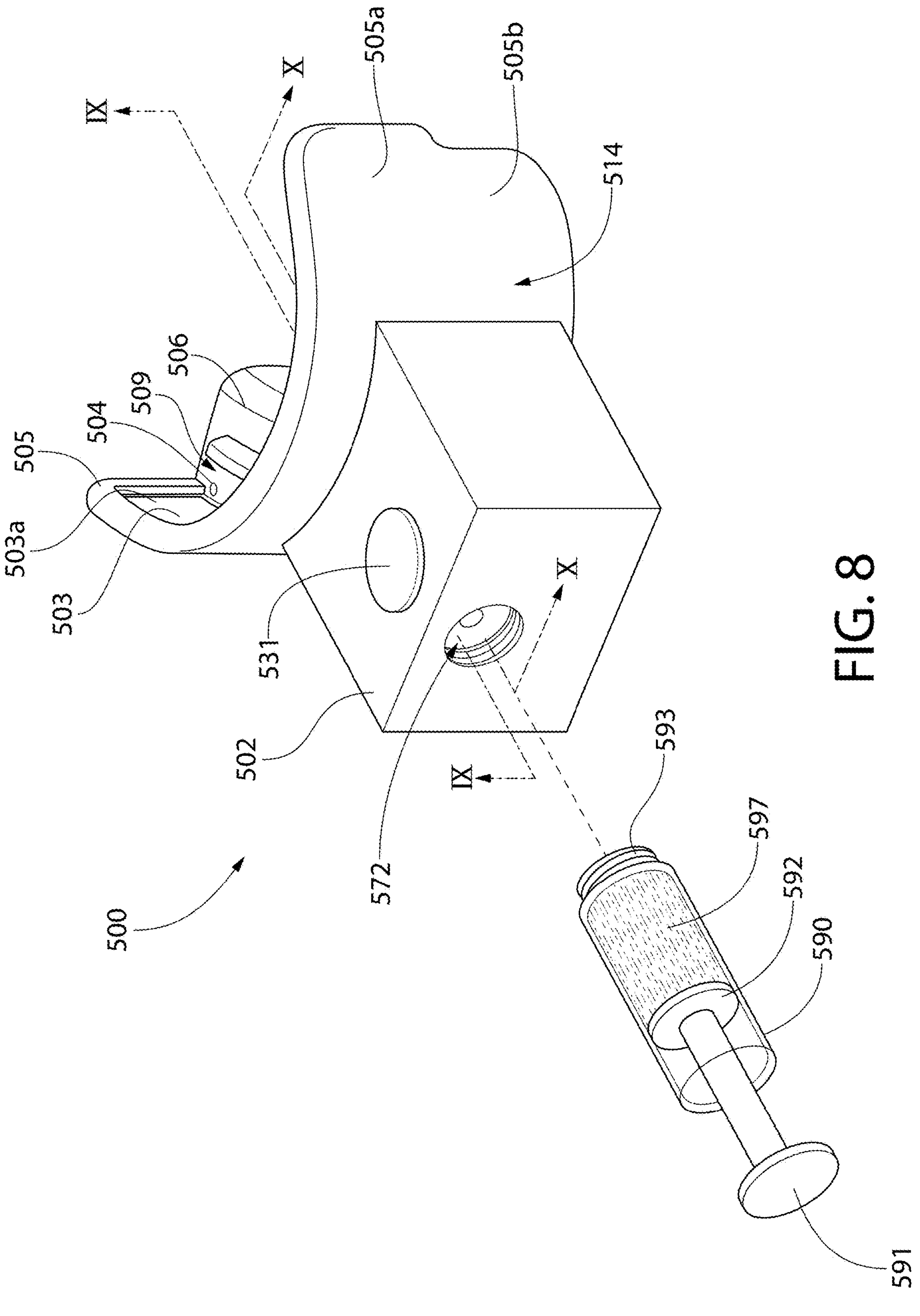
FIG. 8 is a front perspective view of a teeth whitening system in accordance with a second embodiment of the present invention.
Figure 9:
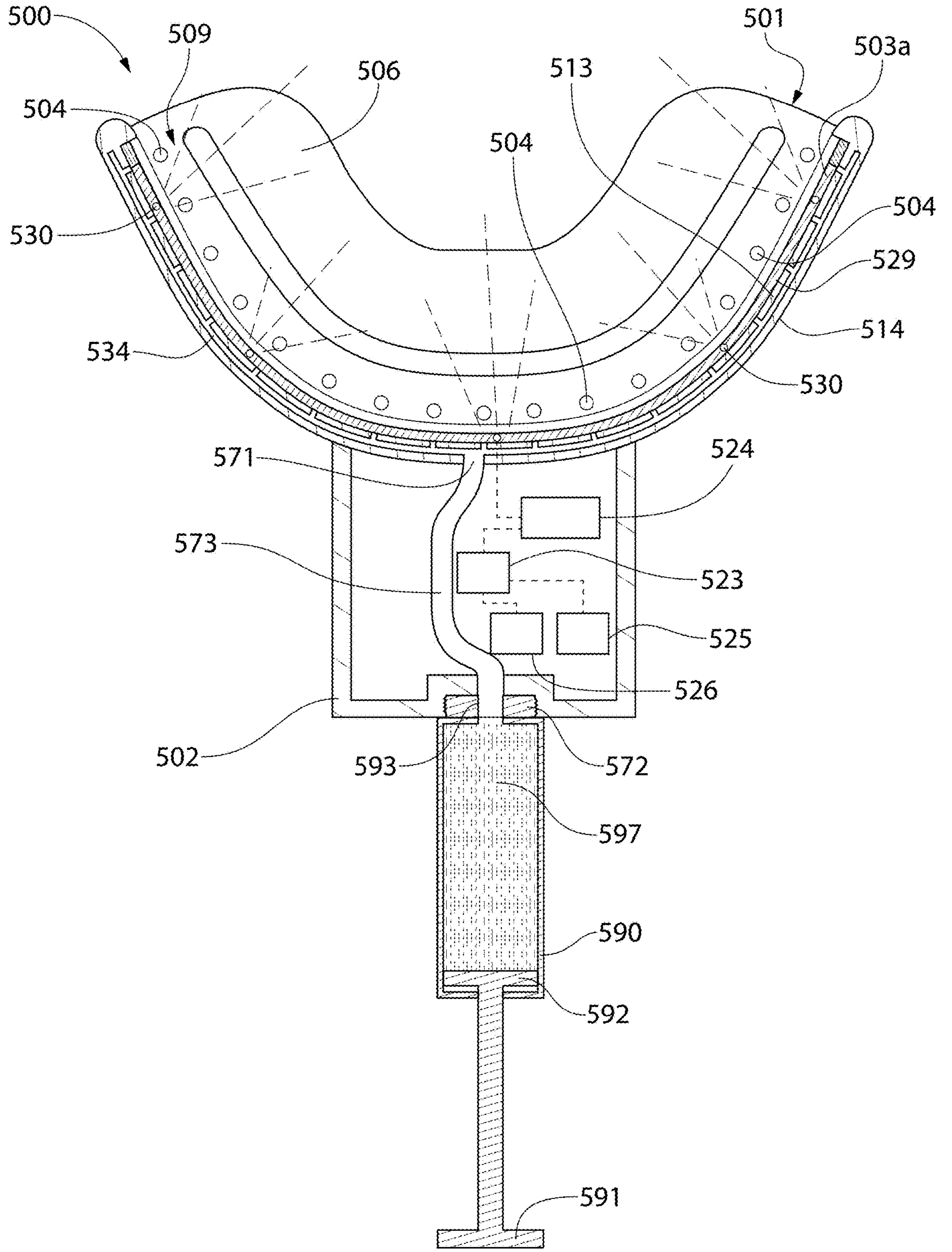
FIG. 9 is a cross-sectional view taken along line IX-IX of FIG. 8 illustrating an electromagnetic radiation source coupled to a mouthpiece and emitting electromagnetic radiation and a container containing a tooth whitening material coupled to the mouthpiece.
Figure 10:
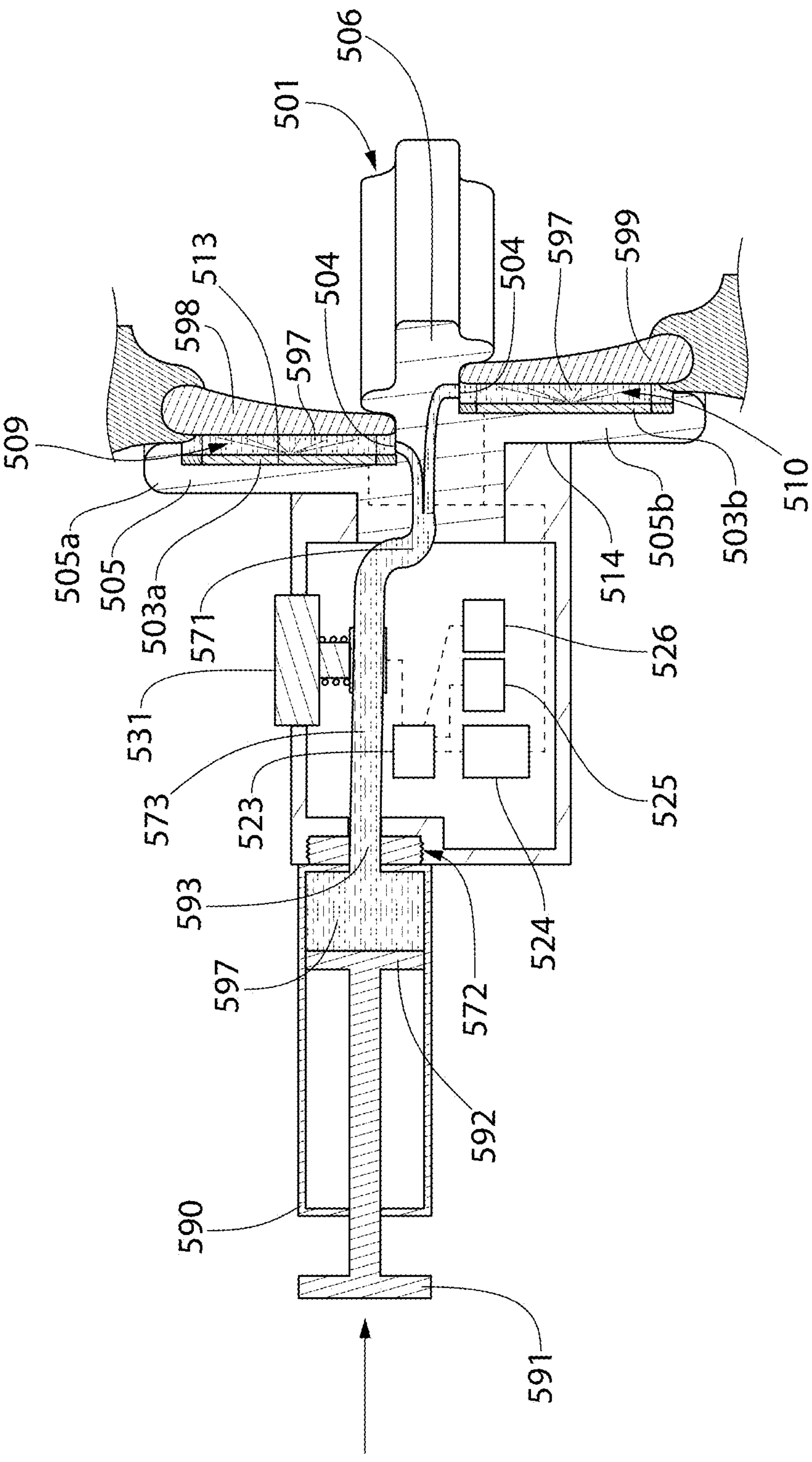
FIG. 10 is a cross-sectional view taken along line X-X of FIG. 8, wherein a user's teeth are engaged with the mouthpiece and the tooth whitening material has been dispensed into contact with the user's teeth.

Referring now to FIGS. 8-10 concurrently, a teeth whitening system 500 will be described in accordance with another embodiment of the present invention. The teeth whitening system 500 is similar to the teeth whitening systems 100, 200, 300, 400 described herein above. Thus, features of the teeth whitening system 500 that are similar to features of the teeth whitening systems 100, 200, 300, 400 will be similarly numbered except that the 500-series of numbers will be used. Certain features of the teeth whitening system 500 that have already been described above with regard to the teeth whitening systems 100, 200, 300, 400 will not be described herein below in the interest of brevity, it being understood that the description of the teeth whitening systems 100, 200, 300, 400 provided above applies. Thus, for features of the tooth whitening system 500 that are numbered but not described, the description of the similar feature of the tooth whitening systems 100, 200, 300, 400 applies.

The teeth whitening system 500 generally comprises a mouthpiece 501, a housing 502 coupled to and extending from the mouthpiece 501, and first and second electromagnetic radiation sources 503*a*, 503*b* coupled to the mouthpiece 501. The mouthpiece 501 comprises a wall 505 comprising an upper wall portion 505*a* and a lower wall portion 505*b*, and a bite platform 506 extending from the wall 505 between the upper and lower wall portions 505*a*, 505*b*. The wall 505 has an inner surface 513 and an opposing outer surface 514. Furthermore, the mouthpiece 501 also comprises a distribution manifold 534 that is fluidly coupled to a plurality of apertures 504. The details of the distribution manifold 534 and the plurality of apertures 504 and their locations within the mouthpiece 501 are the same as that described above with regard to the teeth whitening system 100. The electrical components located within the housing 502 include an actuator 531, a processor 523, a power source 524, a timer 525, and a heater 526 that are operably coupled together in the manner described herein above with regard to the teeth whitening system 100.

In this embodiment, the housing 502 does not also house a reservoir and pump system for dispensing the tooth whitening material into the channels 509, 510 and into contact with the user's teeth 598, 599 within the channels 509, 510. Rather, in this embodiment an opening 571 is formed into the outer surface 514 of the wall 505 and forms a passageway from the external environment to the distribution manifold 534. Thus, the tooth whitening material 597 can be injected into the mouthpiece 501 through the opening 571, into the distribution manifold 534, and out through the apertures 504 for dispensing onto the first and second channels 509, 510.

In the embodiment exemplified in FIGS. 8-10, the opening 571 is formed into the wall 505 of the mouthpiece 501 on a location of the mouthpiece 501 from which the housing 502 extends. Thus, in this embodiment an opening 572 is also formed into the housing 502, and a fluid pathway 573 extends through the housing 502 and fluidly couples the opening 572 in the housing 502 to the opening 571 in the wall 505 of the mouthpiece 501. Thus, in this embodiment the tooth whitening material 597 is injected through the opening 572 in the housing 502, passes through the housing 502 within the fluid pathway 573, passes through the opening 571 in the wall 505 of the mouthpiece 501 and into the distribution manifold 534, and passes from the distribution manifold 534 through each of the apertures 504 for dispensing into the first and second channels 509, 510. As can be seen, the fluid pathway 573 is fluidly isolated from the electrical components within the housing 502 so that the tooth whitening material 597 does not come into contact with the electrical components.

In order to dispense the tooth whitening material 597 into the first and second channels 509, 510 as described herein above, the tooth whitening material 597 is packaged within a container 590 that is separate from the mouthpiece 501 and the housing 502. In the exemplified embodiment, the container 590 is a syringe. However, the invention is not to be so limited and the container 590 can be any structure capable of storing and holding a supply of the tooth whitening material 597 and dispensing the tooth whitening material 597 in the manner described herein. Thus, the container 590 can be any type of syringe, bag, capsule, tube, or the like that can inject the tooth whitening material 597 through the openings 571, 572 in the housing 502 and/or mouthpiece 501 for dispensing into contact with the user's teeth 598, 599.

FIG. 9 illustrates the container 590 coupled to the opening 572 formed into the housing 502. In the exemplified embodiment, the container 590 and the opening 572 have mating threaded screw features so that the container 590 can be screwed onto the housing 502. Of course, the invention is not to be so limited in all embodiments and in certain other embodiments the container 590 may be coupled to the opening 572 of the housing 502 using other mechanical means, such as a snap-fit, adhesion, interference fit, fasteners, or the like. Furthermore, in other embodiments the container 590 may simply be manually held within the opening 572 in the housing 502 during dispensing of the tooth whitening material 597 from the container 590 into the mouthpiece 501 and housing 502 without any mechanical coupling therebetween.

In this embodiment, the container 590 may hold a single dose or multiple doses of the tooth whitening material 597, although a single dose may be preferable in certain embodiments. When it is desired to use the teeth whitening system 500, the mouthpiece 501 is inserted into the user's mouth in the same manner as has been described herein above. Once so positioned, a user will bring the container 590 up to the opening 572 in the housing 502 and mechanically couple the container 590 to the opening 572 if means to do so are available, or simply hold the container 590 in place within/against the opening 572. Once so positioned, the user will manually dispense the tooth whitening material 597 from the container 590. In the exemplified embodiment, this can be achieved by a user pressing a plunger top 591 of the container 590 towards the body of the container 590 so that a plunger seal 592 of the container 590 forces the tooth whitening material 597 out through a nozzle 593 of the container 590. The tooth whitening material 597 will exit the container 590 through the nozzle 593, flow through the opening 572 in the housing 502, the fluid pathway 573, and the opening 571 in the wall 505 of the mouthpiece 501, flow through the distribution manifold 534, through the apertures 504, and into the first and second channels 509, 510 for contact with the user's teeth 598, 599.

As noted above, the container 590 may hold a single dose or multiple doses of the tooth whitening material 597. However, it may be preferable for the container 590 to hold a single dose of the tooth whitening material 597 so that the user can dispense the entirety of the tooth whitening material 597 from the container 590 during each use to prevent the user from having to calculate the appropriate amount of the tooth whitening material 597 to dispense. The single dose may be pre-determined based on the width/volume of the first and second channels 509, 510 so that the tooth whitening material 597 completely fills the first and second channels 509, 510 to ensure a thorough and even distribution of the tooth whitening material 597 onto the surfaces of the user's teeth 598, 599 is achieved.

After the tooth whitening material 597 is dispensed into the channels 509, 510 and into contact with the user's teeth 598, 599 as described above, the user can activate the electromagnetic radiation sources 503*a*, 503*b* in any of the manners described herein above to emit the electromagnetic radiation onto the surfaces of the user's teeth 598, 599 that have been contacted or pre-coated with the tooth whitening material 597. This can be achieved by the user pressing an actuation button 531 or in any other manner described herein. Furthermore, the electromagnetic radiation may be emitted for a predetermined period of time and automatically shut off, or may be manually shut off by a user after a desired time period has been reached if so desired.

Figure 11:
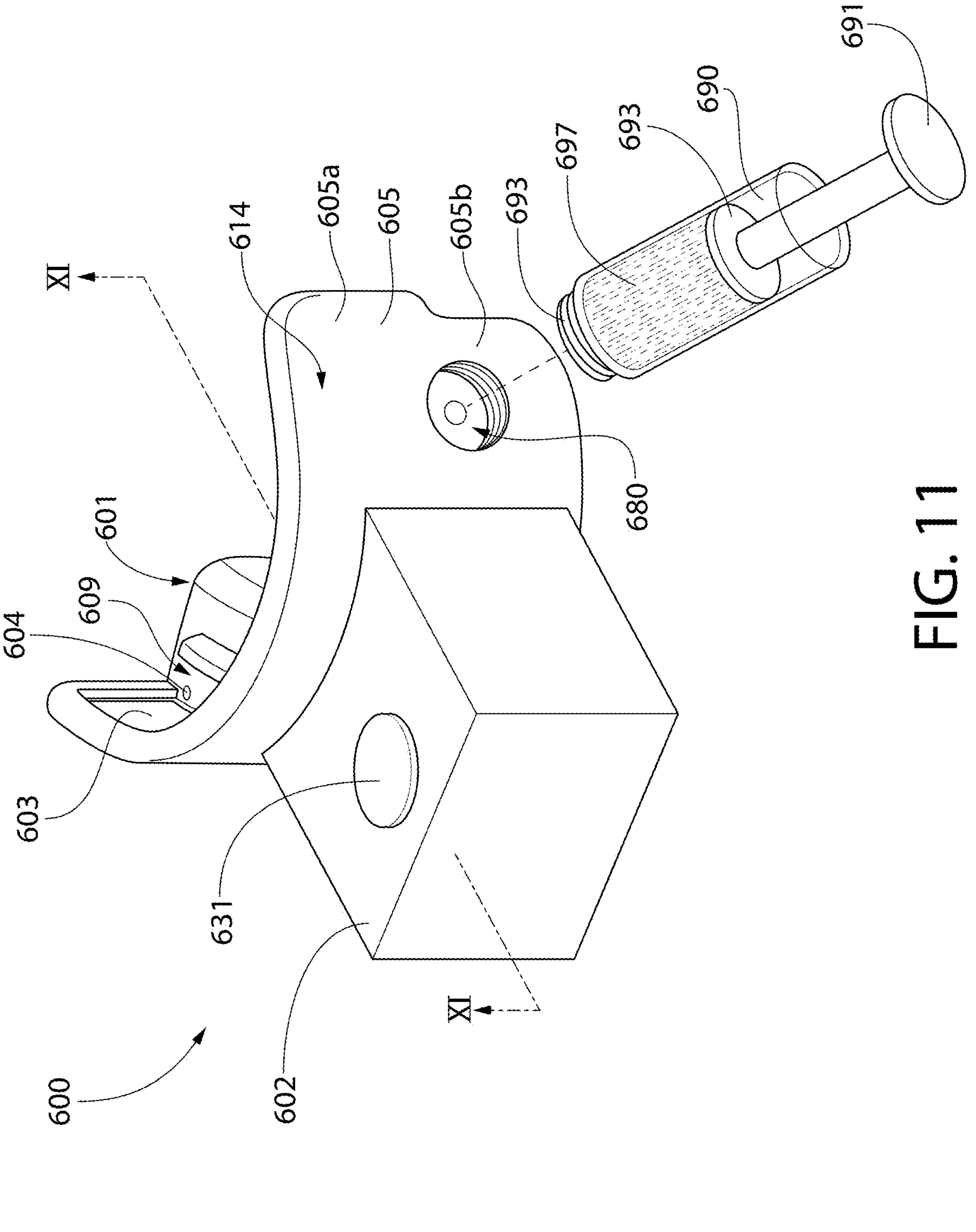
FIG. 11 is a front perspective view of a teeth whitening system in accordance with a third embodiment of the present invention.
Figure 12:
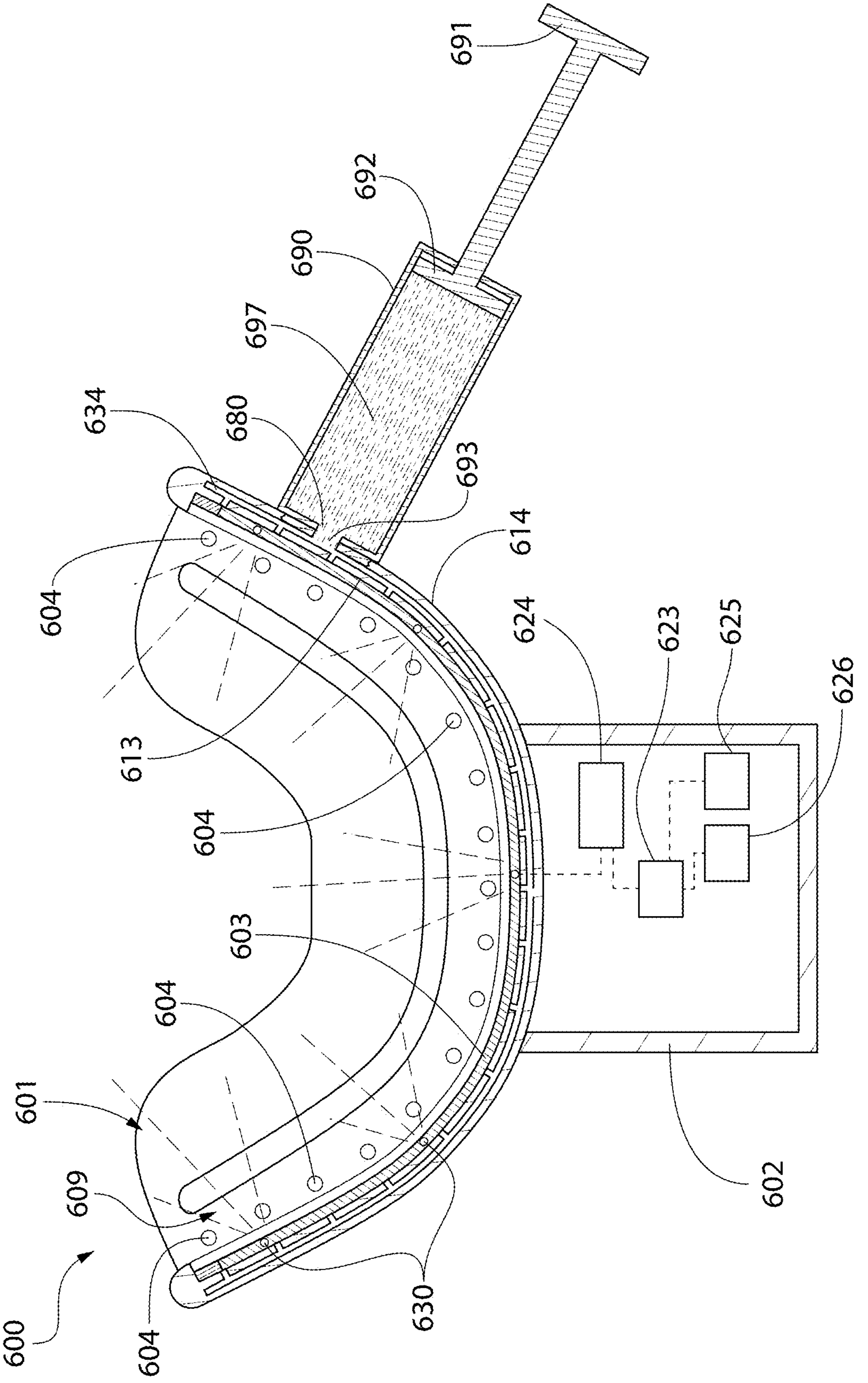
FIG. 12 is a cross-sectional view taken along line XII-XII of FIG. 11 illustrating an electromagnetic radiation source coupled to a mouthpiece and emitting electromagnetic radiation and a container containing a tooth whitening material coupled to the mouthpiece.

Referring now to FIGS. 11 and 12 concurrently, a teeth whitening system 600 will be described in accordance with another embodiment of the present invention. The teeth whitening system 600 is similar to the teeth whitening system 500 described herein above. Thus, features of the teeth whitening system 600 that are similar to features of the teeth whitening system 500 will be similarly numbered except that the 600-series of numbers will be used. Certain features of the teeth whitening system 600 will be numbered in the drawings but not described, and it should be appreciated that the description of those numbered features in the teeth whitening system 500 applies. Certain features of the teeth whitening system 600 that have already been described above with regard to the teeth whitening systems 100, 200, 300, 400, 500 will not be described herein below in the interest of brevity, it being understood that the description of the teeth whitening systems 100, 200, 300, 400, 500 provided above applies. Thus, for features of the tooth whitening system 600 that are numbered but not described, the description of the similar feature of the tooth whitening systems 100, 200, 300, 400, 500 applies.

The teeth whitening system 600 is identical to the teeth whitening system 500 except in the teeth whitening system 600 the tooth whitening material 697 is not dispensed through the housing 602, but rather is dispensed directly into the mouthpiece 601. Specifically, in this embodiment the mouthpiece 601 comprises an opening 680 that forms a passageway from the external environment into the distribution manifold 634, the distribution manifold 634 being fluidly coupled to the plurality of apertures 604. However, in this embodiment the opening 680 is not covered by the housing 602, but rather is exposed directly to the external environment. Thus, during use the mouthpiece 601 is inserted into the user's mouth and the container 690 is aligned with the opening 680 in the rear surface 614 of the wall 605 of the mouthpiece 601. The tooth whitening material 697 is then dispensed from the container 690. In the exemplified embodiment, this is achieved by pressing the plunger top 691 downward which forces the plunger seal 692 to force the tooth whitening material 697 out through the nozzle 693 of the container 690. Of course, other manners of dispensing can be used when the container 690 takes on other forms and is not a syringe as exemplified herein.

Once dispensed from the container 690, the tooth whitening material 697 flows directly through the opening 680 in the wall 605 of the mouthpiece 601 and into the distribution manifold 634. The tooth whitening material 697 continues to flow through the distribution manifold 634 and out through the apertures 604 and into the first and second channels 609, 610 in the same manner as described above with regard to the teeth whitening system 500 of FIGS. 7-10. Thus, the teeth whitening system 600 is the same in operation as the teeth whitening system 500 except that the tooth whitening material 697 is not dispensed through the housing 602, but rather is dispensed directly into the mouthpiece 601.

Any of the above-described teeth whitening systems 100, 200, 300, 400, 500, 600 may include a washout or flushing feature. For example, the mouthpiece or housing may include a flexible slit that allows water or other washout fluid to pass through the distribution manifold to ensure a proper clean-out. In the embodiments of FIGS. 7-10 and 11-12, a container or syringe having a greater volume of water or cleaning solution compared to the volume of the tooth whitening material may be injected into the housing or mouthpiece after use for cleaning. Thus, the water or cleaning solution can be forced through the distribution channel and apertures for cleaning of the device.

The teeth whitening systems 100, 200, 300, 400, 500 may in certain embodiments be sold as a kit that includes the mouthpiece/housing and a supply of the tooth whitening material. In other embodiments the mouthpiece/housing may be sold by itself without tooth whitening material. Furthermore, in certain embodiments the mouthpiece/housing may be used to emit electromagnetic radiation onto the user's teeth without also dispensing the tooth whitening material into contact with the user's teeth. Alternatively, the mouthpiece/housing may be used to dispense the tooth whitening material into contact with the user's teeth without also emitting electromagnetic radiation onto the user's teeth. Thus, there is versatility in the use of the devices and systems described herein. Furthermore, it should be appreciated that when the device is used for both dispensing the tooth whitening material and emitting electromagnetic radiation onto the user's teeth, the tooth whitening material may be optically clear to enable the electromagnetic radiation to be transmitted through the tooth whitening material and onto the surfaces of the user's teeth.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A teeth whitening system comprising:

a mouthpiece comprising:

a wall comprising an inner surface having a first concave curvature and an outer surface opposite the inner surface having a convex curvature, the wall formed of a first material, the wall extending from a proximal end that is coupled to a bite platform to a distal end, wherein the inner surface of the wall comprises a first portion extending from the bite platform to a shoulder, and a second portion extending from the shoulder to the distal end, the first portion of the inner surface of the wall being recessed relative to the second portion of the inner surface of the wall;

an electromagnetic radiation source comprising: a front surface, a rear surface opposite the front surface, a first flexible circuit, and a plurality of first illumination elements embedded within the first flexible circuit that generate light which is emitted from the rear surface of the electromagnetic radiation source;

the electromagnetic radiation source mounted to the first portion of the inner surface of the wall so that the rear surface of the electromagnetic radiation source assumes a first concave curvature, the electromagnetic radiation source operably coupled to a control circuit having a power source; and the bite platform extending from the inner surface of the wall, the bite platform formed of a second material having a hardness that is less than a hardness of the first material.

2. The teeth whitening system according to claim 1 wherein the first flexible circuit comprises a flat, flexible sheet and the plurality of first illumination elements are positioned on or embedded within the flat, flexible sheet.

3. The teeth whitening system according to claim 1 wherein the first flexible circuit is disposed within a recess defined by the first portion of the inner surface of the wall and is covered by a portion of the wall.

4. The teeth whitening system according to claim 1 wherein an exposed surface of the electromagnetic radiation source remains recessed relative to the second portion of the inner surface of the wall.

5. The teeth whitening system according to claim 1 further comprising a first ridge extending upwardly from the bite platform and spaced apart from an upper wall portion of the wall by a first gap, and a second ridge extending downwardly from the bite platform and spaced apart from a lower wall portion of the wall by a second gap, the first and second ridges offset from one another.

6. The teeth whitening system according to claim 1 wherein a transparent or translucent portion of the wall covers the electromagnetic radiation source such that the electromagnetic radiation source is enclosed within the wall of the mouthpiece and light emitted by the electromagnetic radiation source passes through the transparent or translucent portion of the wall.

7. The teeth whitening system according to claim 1 wherein the electromagnetic radiation source comprises at least one thousand of the first illumination elements.

8. The teeth whitening system according to claim 1 wherein the mouthpiece seals a perimeter of the electromagnetic radiation source, a central portion of the electromagnetic radiation source remaining exposed.

9. The teeth whitening system according to claim 1 wherein the electromagnetic radiation source emits the light having a wavelength in a range of 375 nm to 520 nm.

10. The teeth whitening system according to claim 1 wherein the electromagnetic radiation source emits the light having a wavelength in a range of 405 nm to 415 nm.

11. An oral treatment system comprising:

a mouthpiece comprising a wall and a bite platform extending from the wall, the wall of the mouthpiece comprising an upper wall portion extending upward from the bite platform and a lower wall portion extending downward from the bite platform, the upper wall portion comprising an inner surface having a first upper portion extending from the bite platform to an upper shoulder and a second upper portion extending from the upper shoulder to a distal end of the upper wall portion, the first upper portion being recessed relative to the second upper portion, and the lower wall portion comprising an inner surface having a first lower portion extending from the bite platform to a lower shoulder and a second lower portion extending from the lower shoulder to a distal end of the lower wall portion, the first lower portion being recessed relative to the second lower portion, the upper wall portion and an upper surface of the bite platform forming a first channel that is configured to receive a user's upper teeth, the lower wall portion and a lower surface of the bite platform forming a second channel that is configured to receive the user's lower teeth, the bite platform being positioned between the user's upper and lower teeth, the bite platform being formed of a hard rubber and the wall being formed of a food grade polymer;

a first electromagnetic radiation source coupled to the first upper portion of the upper wall portion and configured to emit light onto surfaces of the user's upper teeth that are positioned in the first channel, the first electromagnetic radiation source comprising a first flexible circuit and a plurality of first illumination elements located on the first flexible circuit; and a second electromagnetic radiation source coupled to the first lower portion of the lower wall portion and configured to emit light onto surfaces of the user's lower teeth that are positioned in the second channel, the second electromagnetic radiation source comprising a second flexible circuit and a plurality of second illumination elements located on the second flexible circuit.

12. The oral treatment system according to claim 11 wherein the first and second electromagnetic radiation sources are flexible printed light emitting diodes or flexible organic light emitting diodes.

13. The oral treatment system according to claim 11 wherein the first flexible circuit is a flat, flexible sheet having the first illumination elements positioned thereon or embedded therein, and wherein the second flexible circuit is a flat, flexible sheet having the second illumination elements positioned thereon or embedded therein.

14. The oral treatment system according to claim 11 wherein the upper wall portion comprises an inner surface and the lower wall portion comprises an inner surface, the first electromagnetic source located on the inner surface of the upper wall portion and the second electromagnetic source located on the inner surface of the lower wall portion, and wherein the inner surfaces of the upper and lower wall portions are offset from one another.

15. The oral treatment system according to claim 14 wherein the first electromagnetic radiation source is offset from the second electromagnetic radiation source.

16. The oral treatment system according to claim 15 wherein the first flexible circuit is disposed within a recess defined by the first upper portion of the upper wall portion and the second flexible circuit is entirely disposed within a recess defined by the first lower portion of the lower wall portion.

17. The oral treatment system according to claim 16 wherein transparent or translucent portions of the upper and lower wall portions cover the first and second electromagnetic radiation sources, respectively, such that the first and second electromagnetic radiation sources are enclosed within the upper and lower wall portions and light emitted by the first and second electromagnetic radiation sources passes through the transparent or translucent portions of the upper and lower wall portions.

18. The oral treatment system according to claim 11 wherein the first electromagnetic radiation source and the second electromagnetic radiation source emit light having a wavelength in a range of 405 nm to 415 nm.

19. A teeth whitening system comprising:

a mouthpiece comprising:

a wall and a bite platform extending from the wall that collectively define a channel configured to receive a user's teeth, the bite platform comprising a cavity and being formed of a compressible material;

one or more apertures in the bite platform, the one or more apertures being fluidly coupled to the cavity;

an electromagnetic radiation source coupled to the mouthpiece and configured to emit electromagnetic radiation onto surfaces of the user's teeth positioned in the channel; and a bladder comprising a rupturable material, a tooth whitening material housed within the bladder, the bladder being removably positioned within the cavity of the bite platform, wherein compression of the bite platform ruptures the bladder and dispenses the tooth whitening material from the cavity through the one or more apertures to the channel for contact with the surfaces of the user's teeth.

* * * * *